US006277337B1

(12) United States Patent
Goodrich, Jr. et al.

(10) Patent No.: US 6,277,337 B1
(45) Date of Patent: Aug. 21, 2001

(54) METHOD AND APPARATUS FOR INACTIVATION OF BIOLOGICAL CONTAMINANTS USING PHOTOSENSITIZERS

(75) Inventors: Raymond Paul Goodrich, Jr., Denver; Dennis Hlavinka, Golden; Frank Corbin, III, Littleton; Edward C. Wood, Jr., Lakewood, all of CO (US)

(73) Assignee: Gambro, Inc., Lakewood, CO (US)

( * ) Notice: Subject to any disclaimer, the term of this patent is extended or adjusted under 35 U.S.C. 154(b) by 0 days.

(21) Appl. No.: 09/357,188

(22) Filed: Jul. 20, 1999

Related U.S. Application Data

(63) Continuation-in-part of application No. 09/119,666, filed on Jul. 21, 1998.

(51) Int. Cl.[7] .................................................. B01J 19/08
(52) U.S. Cl. ............................................................. 422/186.3
(58) Field of Search ........................................ 422/186.3

(56) References Cited

U.S. PATENT DOCUMENTS

| Re. 32,874 | 2/1989 | Rock et al. ........................... 424/101 |
| 1,961,700 | 6/1934 | Moehler ................... 167/3 |
| 2,056,614 | 10/1936 | Moehler ................... 21/18 |

(List continued on next page.)

FOREIGN PATENT DOCUMENTS

| 0 196 515 A1 | 3/1986 | (EP) . |
| 0 491 757 B1 | 9/1990 | (EP) . |
| 0 525 138 B1 | 12/1991 | (EP) . |

(List continued on next page.)

OTHER PUBLICATIONS

Friedman, L.I. et al., (1995), "Reducing the infectivity of blood components what we have learned", Immun. Invest. 24(1&2):49–71 No month available.

Ghiron, C.A. and Spikes, J.D., (1965), "The flavin–sensitized photoinactivation of trypsin", Photochem. and Photobio. 4:13–26 No month available.

Hanson, C.V., (Mar. 1979), "Photochemical Inactivation of Deoxyribonucleic and Ribonucleic Acid Viruses by Cholorpromazine", Antimicrob. Agent Chemother, 15(3):461–464 No month available.

Hoffman, M.E. and Meneghini, R., (1979), "DNA strand breaks in mammalian cells exposed to light in the presence of riboflavin and tryptophan", Photochem. and Photobio. 29:299–303 No month available.

(List continued on next page.)

*Primary Examiner*—K. Mayekar
(74) *Attorney, Agent, or Firm*—Greenlee, Winner and Sullivan, P.C.

(57) ABSTRACT

Methods and apparatuses are provided for inactivation of microorganisms in fluids or on surfaces. Preferably the fluids contain blood or blood products and comprise biologically active proteins. Preferred methods include the steps of adding an effective, non-toxic amount of an endogenous photosensitizer to a fluid and exposing the fluid to photoradiation sufficient to activate the endogenous photosensitizer whereby microorganisms are inactivated. Other fluids, including juices, water and the like, may also be decontaminated by these methods as may surfaces of foods, animal carcasses, wounds, food preparation surfaces and bathing and washing vessel surfaces. Alloxazines and K- and L-vitamins are among the preferred photosensitizers. Systems and apparatuses for flow-through and batch processes are also provided for decontamination of such fluids using photosensitizers.

12 Claims, 23 Drawing Sheets

U.S. PATENT DOCUMENTS

| | | | |
|---|---|---|---|
| 2,212,230 | 8/1940 | Goldmann | 250/11 |
| 2,212,330 | 8/1940 | Thomas | 250/52 |
| 3,456,053 | 7/1969 | Crawford | 424/89 |
| 3,776,694 | 12/1973 | Leittl | 21/102 R |
| 3,852,032 | 12/1974 | Urbach | 21/54 |
| 3,926,556 | 12/1975 | Boucher | 21/54 R |
| 4,124,598 | 11/1978 | Hearst et al. | 260/343.21 |
| 4,139,348 | 2/1979 | Swartz | 23/232 E |
| 4,169,204 | 9/1979 | Hearst et al. | 546/270 |
| 4,196,281 | 4/1980 | Hearst et al. | 536/28 |
| 4,312,883 | 1/1982 | Baccichetti et al. | 424/279 |
| 4,398,031 | 8/1983 | Bender et al. | 549/282 |
| 4,421,987 | 12/1983 | Herold | 250/492.1 |
| 4,424,201 | 1/1984 | Valinsky et al. | 424/3 |
| 4,456,512 | 6/1984 | Bieler et al. | 204/162 R |
| 4,474,153 | 10/1984 | Hanamoto . | |
| 4,481,167 | 11/1984 | Ginter et al. | 422/29 |
| 4,493,981 | 1/1985 | Payne | 219/450 |
| 4,568,328 | 2/1986 | King | 604/6 |
| 4,578,056 | 3/1986 | King et al. | 604/6 |
| 4,596,547 | 6/1986 | Troutner | 604/4 |
| 4,604,356 | 8/1986 | Blake, II | 435/194 |
| 4,614,190 | 9/1986 | Stanco et al. | 128/395 |
| 4,623,328 | 11/1986 | Hartranft | 604/4 |
| 4,642,171 | 2/1987 | Sekine et al. | 204/298 |
| 4,645,649 | 2/1987 | Nagao | 422/186.3 |
| 4,648,992 | 3/1987 | Graf et al. | 540/124 |
| 4,649,151 | 3/1987 | Dougherty et al. | 514/410 |
| 4,683,195 | 7/1987 | Mullis et al. | 435/6 |
| 4,683,202 | 7/1987 | Mullis | 435/91 |
| 4,693,981 | 9/1987 | Wiesehahn et al. | 435/238 |
| 4,695,460 | 9/1987 | Holme | 424/101 |
| 4,708,715 | 11/1987 | Troutner et al. | 604/6 |
| 4,737,140 | 4/1988 | Lee et al. | 604/4 |
| 4,788,038 | 11/1988 | Matsunaga | 422/22 |
| 4,861,704 | 8/1989 | Reemtsma et al. | 435/1 |
| 4,866,282 | 9/1989 | Miripol et al. | 250/455.1 |
| 4,878,891 | 11/1989 | Judy et al. | 604/5 |
| 4,880,788 | 11/1989 | Moake et al. | 514/150 |
| 4,921,473 | 5/1990 | Lee et al. | 494/27 |
| 4,946,438 | 8/1990 | Reemtsma et al. | 604/53 |
| 4,961,928 | 10/1990 | Holme et al. | 424/533 |
| 4,992,363 | 2/1991 | Murphy | 435/2 |
| 4,994,367 | 2/1991 | Bode et al. | 435/2 |
| 4,998,931 | 3/1991 | Slichter et al. | 604/20 |
| 5,017,338 | 5/1991 | Surgenor | 422/41 |
| 5,020,995 | 6/1991 | Levy | 433/215 |
| 5,030,200 | 7/1991 | Judy et al. | 604/5 |
| 5,039,483 | 8/1991 | Sieber et al. | 422/28 |
| 5,089,146 | 2/1992 | Carmen et al. | 210/782 |
| 5,089,384 | 2/1992 | Hale | 435/2 |
| 5,092,773 | 3/1992 | Levy | 433/224 |
| 5,114,670 | 5/1992 | Duffey | 422/24 |
| 5,114,957 | 5/1992 | Hendler et al. | 514/356 |
| 5,147,776 | 9/1992 | Koerner, Jr. | 435/2 |
| 5,150,705 | 9/1992 | Stinson | 128/396 |
| 5,166,528 | 11/1992 | Le Vay | 250/455.11 |
| 5,184,020 | 2/1993 | Hearst et al. | 250/455.11 |
| 5,185,532 | 2/1993 | Zabsky et al. | 250/455.11 |
| 5,216,251 | 6/1993 | Matschke | 250/455.11 |
| 5,229,081 | 7/1993 | Suda | 427/186 |
| 5,234,808 | 8/1993 | Murphy | 435/2 |
| 5,236,716 | 8/1993 | Carmen et al. | 424/532 |
| 5,248,506 | 9/1993 | Holme et al. | 424/533 |
| 5,258,124 | 11/1993 | Bolton et al. | 210/748 |
| 5,269,946 | 12/1993 | Goldhaber et al. | 210/767 |
| 5,273,713 | 12/1993 | Levy | 422/22 |
| 5,288,647 | 2/1994 | Zimlich, Jr. et al. | 436/174 |
| 5,304,113 | 4/1994 | Sieber et al. | 604/4 |
| 5,344,752 | 9/1994 | Murphy | 435/2 |
| 5,344,918 | 9/1994 | Dazey et al. | 530/381 |
| 5,358,844 | 10/1994 | Stossel et al. | 435/2 |
| 5,376,524 | 12/1994 | Murphy et al. | 435/2 |
| 5,378,601 | 1/1995 | Gepner-Puszkin | 435/2 |
| 5,427,695 | 6/1995 | Brown | 210/805 |
| 5,459,030 | 10/1995 | Lin et al. | 435/2 |
| 5,466,573 | 11/1995 | Murphy et al. | 435/2 |
| 5,474,891 | 12/1995 | Murphy | 435/2 |
| 5,482,828 | 1/1996 | Lin et al. | 435/2 |
| 5,487,971 | 1/1996 | Holme et al. | 435/2 |
| 5,503,721 | 4/1996 | Hearst et al. | 204/157.6 |
| 5,527,704 | 6/1996 | Wolf, Jr. et al. | 435/283.1 |
| 5,556,958 * | 9/1996 | Carroll et al. | 536/25.3 |
| 5,556,993 | 9/1996 | Wollowitz et al. | 549/282 |
| 5,557,098 | 9/1996 | D'Silva | 250/222.1 |
| 5,569,579 | 10/1996 | Murphy | 435/2 |
| 5,571,666 | 11/1996 | Floyd et al. | 435/2 |
| 5,593,823 | 1/1997 | Wollowitz et al. | 435/2 |
| 5,597,722 | 1/1997 | Chapman et al. | 435/238 |
| 5,622,867 | 4/1997 | Livesey et al. | 436/18 |
| 5,639,376 | 6/1997 | Lee et al. | 210/645 |
| 5,639,382 | 6/1997 | Brown | 210/739 |
| 5,652,096 | 7/1997 | Cimino | 435/6 |
| 5,658,530 | 8/1997 | Dunn | 422/24 |
| 5,658,722 | 8/1997 | Margolis-Nunno et al. | 435/2 |
| 5,683,661 | 11/1997 | Hearst et al. | 422/186.3 |
| 5,683,768 | 11/1997 | Shang et al. | 428/35.2 |
| 5,686,436 | 11/1997 | Van Dyke | 514/171 |
| 5,691,132 | 11/1997 | Wollowitz et al. | 435/2 |
| 5,698,677 | 12/1997 | Eibl et al. | 530/381 |
| 5,702,684 | 12/1997 | McCoy et al. | 424/10.3 |
| 5,712,086 | 1/1998 | Horowitz et al. | 435/2 |
| 5,756,553 | 5/1998 | Iguchi et al. | 514/772.3 |
| 5,772,960 | 6/1998 | Ito et al. | 422/41 |
| 5,789,150 | 8/1998 | Margolis-Nunno et al. | 435/2 |
| 5,798,238 | 8/1998 | Goodrich, Jr. et al. | 435/173.3 |
| 5,798,523 | 8/1998 | Villenueve et al. | 250/234 |
| 5,817,519 | 10/1998 | Zelmanovic et al. | 436/63 |
| 5,827,644 | 10/1998 | Floyd et al. | 435/2 |
| 5,834,198 | 11/1998 | Famulok et al. | 435/6 |
| 5,843,459 | 12/1998 | Wang et al. | 424/231.1 |
| 5,846,961 | 12/1998 | Van Dyke | 514/171 |
| 5,854,967 | 12/1998 | Hearst et al. | 422/186.3 |
| 5,866,074 | 2/1999 | Chapman et al. | 422/82.09 |
| 5,869,701 | 2/1999 | Park et al. | 549/283 |
| 5,871,900 | 2/1999 | Wollowitz et al. | 435/2 |
| 5,876,676 | 3/1999 | Stossel et al. | 422/102 |
| 5,908,742 | 6/1999 | Lin et al. | 435/2 |
| 5,922,278 | 7/1999 | Chapman et al. | 422/22 |
| 5,935,092 | 8/1999 | Sun et al. | 604/4 |
| 5,976,884 | 11/1999 | Chapman et al. | 436/34 |
| 6,020,333 | 2/2000 | Berque | 514/251 |
| 6,087,141 * | 7/2000 | Margolis-Nunno et al. | 435/173.3 |

FOREIGN PATENT DOCUMENTS

| | | |
|---|---|---|
| 0 679 398 A | 11/1995 | (EP) . |
| 2674753 | 10/1992 | (FR) . |
| 2715303 | 7/1995 | (FR) . |
| 2718353 | 10/1995 | (FR) . |
| WO 91/02529 | 3/1991 | (WO) . |
| WO 92/11057 | 7/1992 | (WO) . |
| WO 92/17173 | 10/1992 | (WO) . |
| WO 94/07426 | 4/1994 | (WO) . |
| WO 94/07499 | 4/1994 | (WO) . |
| WO 95/02325 | 1/1995 | (WO) . |
| WO 95/11028 | 4/1995 | (WO) . |
| WO 95/12973 | 5/1995 | (WO) . |
| WO 95/16348 | 6/1995 | (WO) . |
| WO 96/14740 | 5/1996 | (WO) . |
| WO 97/07674 | 3/1997 | (WO) . |
| WO 97/22245 | 6/1997 | (WO) . |

| | | |
|---|---|---|
| WO 97/36581 | 10/1997 | (WO) . |
| WO 97/36634 | 10/1997 | (WO) . |
| WO 98/31219 | 7/1998 | (WO) . |
| WO 99/11305 | 3/1999 | (WO) . |

OTHER PUBLICATIONS

Malik et al., (1990), "New trends in photobiology—bactericidal effects of photoactivated porphyrins—an alternative approach to antimicrobial drugs", J. Photochem. Photobiol. Pt. B:Biology, 5:281–293 No month available.

North et al. ((993), "Photosensitizers as Virucidal Agents", J. Photobiol, 17(2):99–108 No month available.

Kabuta, H. et al., "Inactivation of viruses by dyes and visible light," (1978) Chemical Abstracts 87(1), Abstract No. 400626 No month available.

Kale, H. et al., "Assessment of the genotoxic potential of riboflavin and lumiflavin; B. Effect of light," (1992) Mutation Research 298:17–23 No month available.

Kobayashi et al., "The molecular mechanism of mutation. Photodynamic action of flavins on the RNA–synthesizing system," (1983) Chemical Abstracts 98(1) Abstract No. 1200.

Ennever, J.F. and Speck, W.T., "Short Communication. Photochemical Reactions of Riboflavin: Covalent Binding to DNA and to Poly (dA)•Poly (dT)," (1983) Pediatr. Res. 17:234–236 No month available.

Matthews, J.L. et al., "Photodynamic therapy of viral contaminants with potential for blood banking applications," (1988) Transfusion 28(1):81–83 No month avaialble.

Ennever, J.F. and Speck, W.T., "Short Communication. Photochemical Reactions of Riboflavin: Covalent Binding to DNA and to Poly (Da)•Poly (Dt)," (1983) Pediatr. Res. 17:234–236 No month available.

Product advertisement for "Ultracure 100SS Plus Specifications," EFOS USA, Inc., Williamsville, NY, USA No date available.

Brodie, A.F. and Watanabe, T., "Mode of action of vitamin K in microorganisms," (1966) Vitam. Horm. 24:447–463 No month available.

Chow, C.S. and Barton, J.K., "Recognition of G–U mismatches by tris(4,7–diphenyl–1,10–phenanthroline)rhodium(III)," (1992) Biochemistry 31(24):5423–5429.

Deutsch, E., "Vitamin K in medical practice: adults," (1966) Vitam. Horm. 24:665–680 No month available.

Joshi, P.C., "Comparison of the DNA–damaging property of photosensitized riboflavin via singlet oxygen ($^1O_2$) and superoxide radical ($O_i^-$) mechanisms," (1985) Toxicology Letters 26:211–217.

Klebanoff, M.A. et al., "The risk of childhood cancer after neonatal exposure to vitamin K," (1993) New Engl. J. Med. 329(13):905–908 No month available.

Korycka–Dahl, M. and Richardson, T., "Photodegradation of DNA with fluorescent light in the presence of riboflavin, and photoprotection by flavin triplet–state quenchers," (1980) Biochimica et Biophysica Acta 610:229–234.

Leontis, N.B. and Westhof, E., "The 5S rRNA loop E: chemical probing and phylogenetic data versus crystal structure," (1998) RNA 4:1134–1153.

Lim, A.C. and Barton, J.K., "Chemical probing of tDNA$^{Phe}$ with transition metal complexes: a structural comparison of RNA and DNA," (1993) Biochemistry 32:11029–11034.

Maddox, J., "The working of vitamin K," (1991) Nature 353(6346):695 No month available.

McCord, E.F., "Chemically induced dynamic nuclear polarization studies of yeast," (1984) Biochemistry 23:1935–1939 No month available.

Merenstein, G.B. et al. (Vitamin K Ad Hoc Task Force), "Controversies concerning vitamin K and the newborn," (1993) Pediatrics 91(5):1001–1003 No month available.

Merrifield, L.S. and Yang, H.Y., "Factors affecting the antimicrobial activity of vitamin K5," (1965) Appl. Microbiol. 13(5):766–770 No month available.

Merrifield, L.S. and Yang, H.Y., "Vitamin K5 as a fungistatic agent," (1965) Applied Microbiol. 13(5):660–662 No month available.

Murata, A. et al., "Effect of vitamins other than vitamin C on viruses: virus–inactivating activity of vitamin K5," (1983) J. Nutr. Sci. Vitaminol (Tokyo) 29(6):721–724 No month available.

Naseem, I. et al., "Effect of alkylated and intercalated DNA on the generation of superoxide anion by riboflavin," (1988) Bioscience Reports 8(5):485–492 No month available.

Pratt, R. et al., "Vitamin $K_5$ as an Antimicrobial Medicament and Preservative," (1950) J. Am. Pharm. Ass'n 39(3):127–134 No month available.

Shwartzman, G., "Antibacterial Properties of 4–Amino–2–Methyl–1–Naphthol Hydrochloride," (1948) Proc. Soc. Exp. Biol. Med. 67:376–378 No month available.

Spranger, J., "Does vitamin K cause cancer?" (1993) Eur. J. Pediatr. 152(2):174 No month available.

Vest, M., "Vitamin K in medical practice: pediatrics," (1966) Vitam. Horm. 24:649–663 No month available.

Yang, H.Y. et al., "Vitamin $K_5$ as a Food Preservative," (1958) Food Technology 501–504 No month available.

* cited by examiner

METHOD AND APPARATUS FOR INACTIVATION OF BIOLOGICAL CONTAMINANTS USING PHOTOSENSITIZERS

CROSS-REFERENCE TO RELATED APPLICATIONS

This application is a continuation-in-part of U.S. application Ser. No. 09/119,666 filed Jul. 21, 1998, still pending which is incorporated herein in its entirety to the extent not incompatible herewith.

BACKGROUND

Contamination of blood supplies with infectious microorganisms such as HIV, hepatitis and other viruses and bacteria presents a serious health hazard for those who must receive transfusions of whole blood or administration of various blood components such as platelets, red cells, blood plasma, Factor VIII, plasminogen, fibronectin, antithrombin III, cryoprecipitate, human plasma protein fraction, albumin, immune serum globulin, prothrombin complex plasma growth hormones, and other components isolated from blood. Blood screening procedures may miss contaminants, and sterilization procedures which do not damage cellular blood components but effectively inactivate all infectious viruses and other microorganisms have not heretofore been available.

Solvent detergent methods of blood component decontamination work by dissolving phospholipid membranes surrounding viruses such as HIV, and do not damage protein components of blood; however, if blood cells are present, such methods cannot be used because of damage to cell membranes.

The use of photosensitizers, compounds which absorb light of a defined wavelength and transfer the absorbed energy to an energy acceptor, has been proposed for blood component sterilization. For example, European Patent application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red, and methylene blue, as blood additives. Protoporphyrin, which occurs naturally within the body, can be metabolized to form a photosensitizer; however, its usefulness is limited in that it degrades desired biological activities of proteins. Chlorpromazine, is also exemplified as one such photosensitizer; however its usefulness is limited by the fact that it should be removed from any fluid administered to a patient after the decontamination procedure because it has a sedative effect.

Goodrich, R. P., et al. (1997), "The Design and Development of Selective, Photoactivated Drugs for Sterilization of Blood Products," Drugs of the Future 22:159–171 provides a review of some photosensitizers including psoralens, and some of the issues of importance in choosing photosensitizers for decontamination of blood products. The use of texaphyrins for DNA photocleavage is described in U.S. Pat. No. 5,607,924 issued Mar. 4, 1997 and 5,714,328 issued Feb. 3, 1998 to Magda et al. The use of sapphyrins for viral deactivation is described in U.S. Pat. No. 5,041,078 issued Aug. 20, 1991 to Matthews, et al. Inactivation of extracellular enveloped viruses in blood and blood components by Phenthiazin-5-ium dyes plus light is described in U.S. Pat. No. 5,545,516 issued Aug. 13, 1996 to Wagner. The use of porphyrins, hematoporphyrins, and merocyanine dyes as photosensitizing agents for eradicating infectious contaminants such as viruses and protozoa from body tissues such as body fluids is disclosed in U.S. Pat. No. 4,915,683 issued Apr. 10, 1990 and related U.S. Pat. No. 5,304,113 issued Apr. 19, 1994 to Sieber et al. The mechanism of action of such photosensitizers is described as involving preferential binding to domains in lipid bilayers, e.g. on enveloped viruses and some virus-infected cells. Photoexcitation of membrane-bound agent molecules leads to the formation of reactive oxygen species such as singlet oxygen which causes lipid peroxidation. A problem with the use of such photosensitizers is that they attack cell membranes of desirable components of fluids to be decontaminated, such as red blood cells, and the singlet oxygen also attacks desired protein components of fluids being treated. U.S. Pat. 4,727,027 issued Feb. 23, 1988 to Wiesehahn, G. P., et al. discloses the use of furocoumarins including psoralen and derivatives for decontamination of blood and blood products, but teaches that steps must be taken to reduce the availability of dissolved oxygen and other reactive species in order to inhibit denaturation of biologically active proteins. Photoinactivation of viral and bacterial blood contaminants using halogenated coumarins is described in U.S. Pat. No. 5,516,629 issued May 14, 1996 to Park, et al. U.S. Pat. No. 5,587,490 issued Dec. 24, 1996 to Goodrich Jr., R. P., et al. and U.S. Pat. No. 5,418,130 to Platz, et al. disclose the use of substituted psoralens for inactivation of viral and bacterial blood contaminants. The latter patent also teaches the necessity of controlling free radical damage to other blood components. U.S. Pat. No. 5,654,443 issued Aug. 5, 1997 to Wollowitz et al. teaches new psoralen compositions used for photodecontamination of blood. U.S. Pat. No. 5,709,991 issued Jan. 20, 1998 to Lin et al. teaches the use of psoralen for photodecontamination of platelet preparations and removal of psoralen afterward. U.S. Pat. No. 5,120,649 issued June 9, 1992 and related U.S. Pat. No. 5,232,844 issued Aug. 3, 1993 to Horowitz, et al., also disclose the need for the use of "quenchers" in combination with photosensitizers which attack lipid membranes, and U.S. Pat. No. 5,360,734 issued Nov. 1, 1994 to Chapman et al. also addresses this problem of prevention of damage to other blood components.

Photosensitizers which attack nucleic acids are known to the art. U.S. Patent 5,342,752 issued Aug. 30, 1994 to Platz et al. discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. This patent fails to disclose an apparatus for decontaminating blood on a flow-through basis. U.S. Pat. No. 5,798,238 to Goodrich, Jr., et al., discloses the use of quinolone and quinolone compounds for inactivation of viral and bacterial contaminants.

Binding of DNA with photoactive agents has been exploited in processes to reduce lymphocytic populations in blood as taught in U.S. Pat. No. 4,612,007 issued Sep. 16, 1986 and related U.S. Pat. No. 4,683,889 issued Aug. 4, 1987 to Edelson.

Riboflavin (7,8-dimethyl-10-ribityl isoalloxazine) has been reported to attack nucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360–363; and Speck, W. T. et al. (1976), "Further Observations on the Photooxidation of DNA in the Presence of Riboflavin," Biochimica et Biophysica Acta 435:39–44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207–217. Hoffmann, M. E., et al. (1979), "DNA Strand Breaks in Mammalian Cells Exposed to Light in the Presence of Riboflavin and Tryptophan," Photochemistry and Photobiology 29:299–303 describes the use of riboflavin and tryptophan to induce breaks in DNA of mammalian cells after exposure to visible fluorescent light or near-ultraviolet light. The article states that these effects did not occur if either riboflavin or tryptophan was omitted from the medium. DNA strand breaks upon exposure to proflavine and light are reported in Piette, J. et al. (1979), "Production of Breaks in Single- and Double-Stranded Forms of Bacteriophage ΦX174 DNA by Proflavine and Light Treatment," Photochemistry and Photobiology 30:369–378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325–333.

J. Cadet, et al. (1983), "Mechanisms and Products of Photosensitized Degradation of Nucleic Acids and Related Model Compounds," Israel J. Chem. 23:420–429, discusses the mechanism of action by production of singlet oxygen of rose bengal, methylene blue, thionine and other dyes, compared with mechanisms not involving production of singlet oxygen by which nucleic acid attack by flavin or pteron derivatives proceeds. Riboflavin is exemplified in this disclosure as having the ability to degrade nucleic acids. Korycka-Dahl, M., et al. (1980), "Photodegradation of DNA with Fluorescent Light in the Presence of Riboflavin, and Photoprotection by Flavin Triplet-State Quenchers," Biochimica et Biophysica Acta 610:229–234 also discloses that active oxygen species are not directly involved in DNA scission by riboflavin. Peak, J. G., et al. (1984), "DNA Breakage Caused by 334-nm Ultraviolet Light is Enhanced by Naturally Occurring Nucleic Acid Components and Nucleotide Coenzymes," Photochemistry and Photobiology 39:713–716 further explores the mechanism of action of riboflavin and other photosensitizers. However, no suggestion is made that such photosensitizers be used for decontamination of medical fluids.

Apparatuses for decontamination of blood have been described in U.S. Pat. No. 5,290,221 issued Mar. 1, 1994 to Wolfe, Jr., et al. and U.S. Pat. No. 5,536,238 issued Jul. 16, 1996 to Bischof. U.S. Pat. No. 5,290,221 discloses the irradiation of fluid in a relatively narrow, arcuate gap. U.S. Pat. 5,536,238 discloses devices utilizing optical fibers extending into a filtration medium. Both patents recommend as photosensitizers benzoporphryin derivatives which have an affinity for cell walls.

All publications referred to herein are hereby incorporated by reference to the extent not inconsistent herewith.

SUMMARY

Methods and apparatuses are provided for treating a fluid or other material to inactivate at least some of the microorganisms and white cells which may be present therein or thereon. Such fluids may also contain one or more components selected from the group consisting of protein, e.g. biologically active protein such as a therapeutic protein, blood and blood constituents, without destroying the biological activity of such components. The methods comprise:

(a) mixing an effective non-toxic amount of an endogenous photosensitizer or endogenously-based derivative photosensitizer with the fluid;

(b) exposing the fluid to photoradiation sufficient to activate the photosensitizer; whereby at least some of the microorganisms are inactivated.

One mechanism by which these photosensitizers may inactivate microorganisms is by interfering with nucleic acids, so as to prevent replication of the nucleic acid.

As used herein, the term "inactivation of a microorganism" means totally or partially preventing the microorganism from replicating, either by killing the microorganism or otherwise interfering with its ability to reproduce.

Microorganisms include viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include ΦX174, Φ6, λ, R17, $T_4$, and $T_2$.

Exemplary bacteria include *P. aeruginosa, S. aureus, S. epidernis, L. monocytogenes, E. coli, K pneumonia* and *S. marcescens*.

Inactivation of white blood cells may be desirable when suppression of immune or autoimmune response is desired, e.g., in processes involving transfusion of red cells, platelets or plasma when donor white blood cells may be present.

Materials which may be treated by the methods of this invention include any materials which are adequately permeable to photoradiation to provide sufficient light to achieve viral inactivation, or which can be suspended or dissolved in fluids which have such permeability to photoradiation. Examples of such materials are whole blood and aqueous compositions containing biologically active proteins derived from blood or blood constituents. Packed red cells, platelets and plasma (fresh or fresh frozen plasma) are exemplary of such blood constituents. In addition, therapeutic protein compositions containing proteins derived from blood, such as fluids containing biologically active protein useful in the treatment of medical disorders, e.g. factor VIII, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen streptokinase complex, ceruloplasmin, transferrin, haptoglobin, antitrypsin and prekallikrein may be treated by the decontamination methods of this invention. Other fluids which could benefit from the treatment of this invention are peritoneal solutions used for peritoneal dialysis which are sometimes contaminated during connection, leading to peritoneal infections.

The term "biologically active" means capable of effecting a change in a living organism or component thereof. "Biologically active" with respect to "biologically active protein" as referred to herein does not refer to proteins which are part of the microorganisms being inactivated. Similarly, "non-toxic" with respect to the photosensitizers means low or no toxicity to humans and other mammals, and does not mean non-toxic to the microorganisms being inactivated. "Substantial destruction" of biological activity means at least as much destruction as is caused by porphyrin and porphyrin derivatives, metabolites and precursors which are known to have a damaging effect on biologically active proteins and cells of humans and mammals.

Similarly, "substantially non-toxic" means less toxic than porphyrin, porphyrin derivatives, metabolites and precursors that are known for blood sterilization.

The term "blood product" as used herein includes blood constituents and therapeutic protein compositions containing proteins derived from blood as defined above. Fluids containing biologically active proteins other than those derived from blood may also be treated by the methods of this invention.

Decontamination methods of this invention using endogenous photosensitizers and endogenously-based photosensitizer derivatives do not substantially destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid. So long as fluid components retain sufficient biological activity to be useful for their intended or natural purposes, their biological activities are not considered to be "substantially destroyed."

The photosensitizers useful in this invention include any photosensitizers known to the art to be useful for inactivating microorganisms. A "photosensitizer" is defined as any compound which absorbs radiation of one or more defined wavelengths and subsequently utilizes the absorbed energy to carry out a chemical process. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Photosensitizers of this invention may include compounds which preferentially adsorb to nucleic acids, thus focusing their photodynamic effect upon microorganisms and viruses with little or no effect upon accompanying cells or proteins. Other photosensitizers are also useful in this invention, such as those using singlet oxygen-dependent mechanisms. Most preferred are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1–5) alkyl or halogen substituents of the photosensitizers from which they are derived, and which preserve the function and substantial non-toxicity thereof. When endogenous photosensitizers are used, particularly when such photosensitizers are not inherently toxic or do not yield toxic photoproducts after photoradiation, no removal or purification step is required after decontamination, and treated product can be directly returned to a patient's body or administered to a patient in need of its therapeutic effect. Preferred endogenous photosensitizers are:

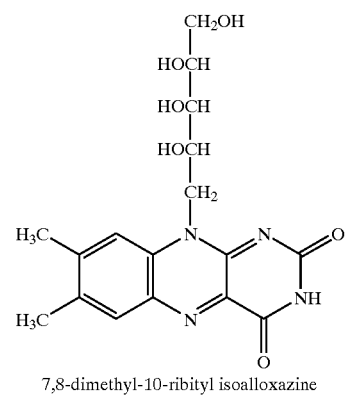

7,8-dimethyl-10-ribityl isoalloxazine

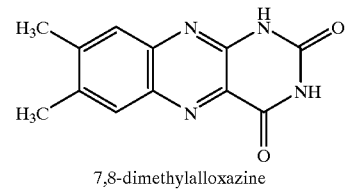

7,8-dimethylalloxazine

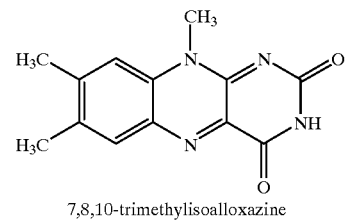

7,8,10-trimethylisoalloxazine

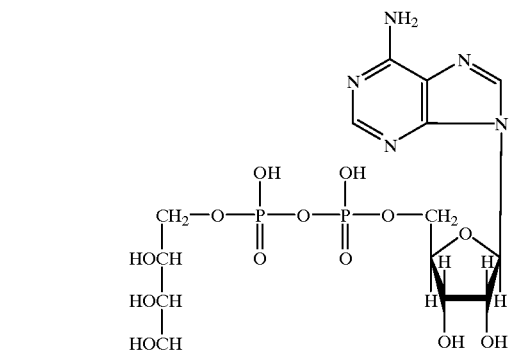

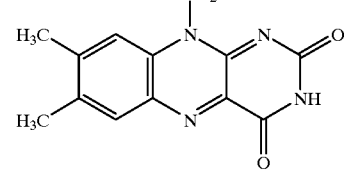

Isoalloxazine-adenine dinucleotide

-continued

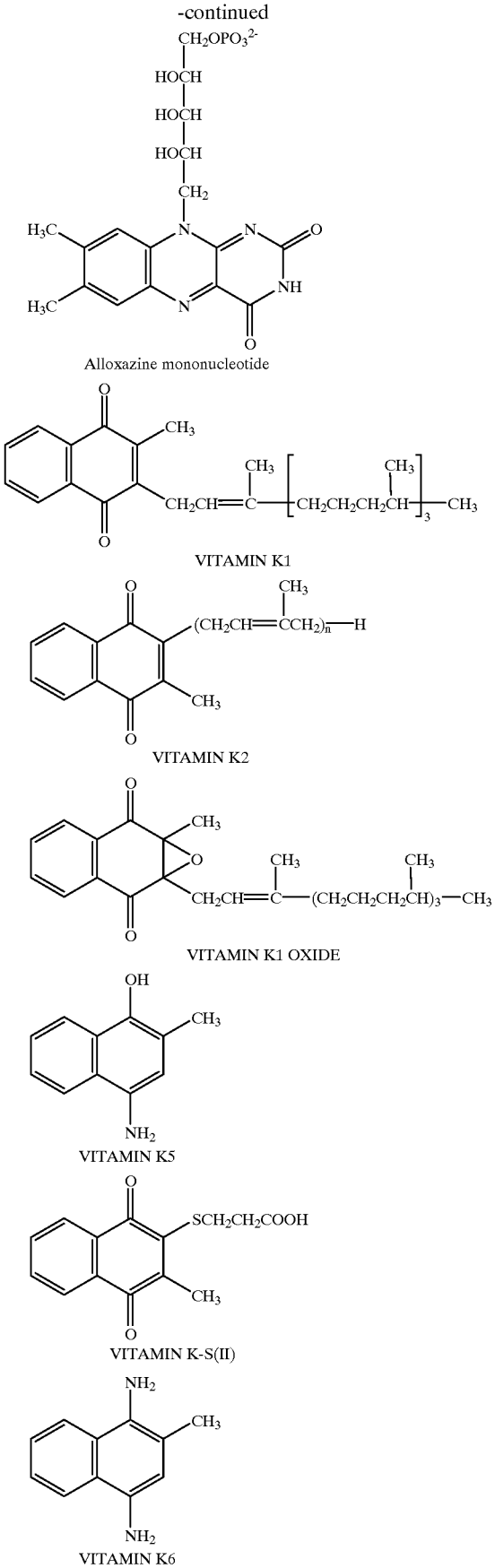

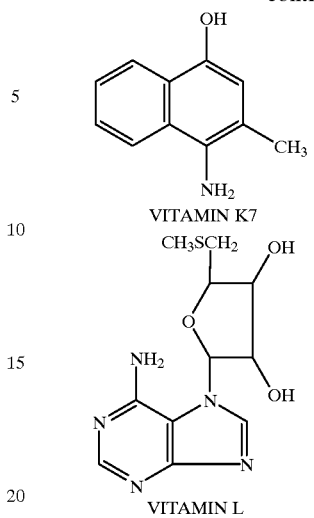

The method of this invention requires mixing the photosensitizer with the material to be decontaminated. Mixing may be done by simply adding the photosensitizer or a solution containing the photosensitizer to a fluid to be decontaminated. In one embodiment, the material to be decontaminated to which photosensitizer has been added is flowed past a photoradiation source, and the flow of the material generally provides sufficient turbulence to distribute the photosensitizer throughout the fluid to be decontaminated. In another embodiment, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate microorganisms therein, but less than a toxic (to humans or other mammals) or insoluble amount. As taught herein, optimal concentrations for desired photosensitizers may be readily determined by those skilled in the art without undue experimentation. Preferably the photosensitizer is used in a concentration of at least about 1 $\mu$M up to the solubility of the photosensitizer in the fluid, and preferably about 10 $\mu$M. For 7,8-dimethyl-10-ribityl isoalloxazine a concentration range between about 1 $\mu$M and about 160 $\mu$M is preferred, preferably about 10 $\mu$M.

The fluid containing the photosensitizer is exposed to photoradiation of the appropriate wavelength to activate the photosensitizer, using an amount of photoradiation sufficient to activate the photosensitizer as described above, but less than that which would cause non-specific damage to the biological components or substantially interfere with biological activity of other proteins present in the fluid. The wavelength used will depend on the photosensitizer selected, as is known to the art or readily determinable without undue experimentation following the teachings hereof. Preferably the light source is a fluorescent or luminescent source providing light of about 300 nm to about 700 nm, and more preferably about 340 nm to about 650 nm of radiation. Wavelengths in the ultraviolet to visible range are useful in this invention. The light source or sources may provide light in the visible range, light in the ultraviolet range, or preferably a mixture of light in the visible and ultraviolet ranges, more preferably about half in the visible and half in the ultraviolet spectrum, although other ratios could be used. One benefit of a mixture of light is that the visible spectrum does not damage platelets but reduces the amount of the more harmful ultraviolet radiation required.

The activated photosensitizer is capable of inactivating the microorganisms present, such as by interfering to prevent their replication. Specificity of action of the photosensitizer is conferred by the close proximity of the photosensitizer to the nucleic acid of the microorganism and this may result from binding of the photosensitizer to the nucleic acid. "Nucleic acid" includes ribonucleic acid (RNA) and deoxyribonucleic acid (DNA). Other photosensitizers may act by binding to cell membranes or by other mechanisms. The photosensitizer may also be targeted to the microorganism to be inactivated by covalently coupling to an antibody, preferably a specific monoclonal antibody to the microorganism.

The fluid containing the photosensitizer may be flowed into a photopermeable container for irradiation. The term "container" refers to a closed or open space, which may be made of rigid or flexible material, e.g., may be a bag or box or trough. It may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima™ Spectra™ and apheresis systems of Cobe Laboratories, Inc., have been used to exemplify another embodiment involving batch-wise treatment of the fluid.

The term "photopermeable" means the material of the container is adequately transparent to photoradiation of the proper wavelength for activating the photosensitizer. In the flow-through system, the container has a depth (dimension measured in the direction of the radiation from the photoradiation source) sufficient to allow photoradiation to adequately penetrate the container to contact photosensitizer molecules at all distances from the light source and ensure inactivation of microorganisms in the fluid to be decontaminated, and a length (dimension in the direction of fluid flow) sufficient to ensure a sufficient exposure time of the fluid to the photoradiation. The materials for making such containers, depths and lengths of containers may be easily determined by those skilled in the art without undue experimentation following the teachings hereof, and together with the flow rate of fluid through the container, the intensity of the photoradiation and the absorptivities of the fluid components, e.g., plasma, platelets, red blood cells, will determine the amount of time the fluid needs to be exposed to photoradiation. For 7,8-dimethyl-10-ribityl isoalloxazine, a preferred amount of radiation is between about $1 J/cm^2$ to $120 J/cm^2$.

In another embodiment involving batch-wise treatment, the fluid to be treated is placed in a photopermeable container which is agitated and exposed to photoradiation for a time sufficient to substantially inactivate the microorganisms. The photopermeable container is preferably a blood bag made of transparent or semitransparent plastic, and the agitating means is preferably a shaker table. The photosensitizer may be added to the container in powdered or liquid form and the container agitated to mix the photosensitizer with the fluid and to adequately expose all the fluid to the photoradiation to ensure inactivation of microorganisms.

Photosensitizer may be added to or flowed into the photopermeable container separately from the fluid being treated or may be added to the fluid prior to placing the fluid in the container. In one embodiment, photosensitizer is added to anticoagulant and the mixture of photosensitizer and anticoagulant are added to the fluid.

Enhancers may also be added to the fluid to make the process more efficient and selective. Such enhancers include antioxidants or other agents to prevent damage to desired fluid components or to improve the rate of inactivation of microorganisms and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, and mixtures thereof.

This invention also comprises fluids comprising biologically active protein, blood or blood constituents and also containing endogenous photosensitizer, endogenously-based derivative photosensitizer, or photoproduct thereof made by the method of claim 1. The fluid may also contain inactivated microorganisms.

In addition to decontamination of whole blood, fluids containing blood products and biologically active proteins, this method is useful for treating other fluids including fluids which are meant for nourishment of humans or animals such as water, fruit, juices, milk, broths, soups and the like. The method is also useful for treating peritoneal or parenteral solutions.

This invention also includes methods for treating surfaces to inactivate microorganisms which may be present thereon comprising applying to such surfaces an inactivation-effective, non-toxic amount of an endogenous photosensitizer or endogenously-based photosensitizer derivative and exposing the surface to photoradiation sufficient to activate the photosensitizer. The surface may be a food surface such as a fruit, vegetable or animal carcass, surface or surfaces of cut or processed foods. Particulate materials such as ground meats may be treated by mixing the photosensitizer with the material and continuing to mix while irradiating to expose fresh surfaces to photoradiation.

The surface may alternatively be a food preparation surface such as a counter top or storage shelf, or may be a surface of a bathing or washing vessel such as a kitchen sink, bathtub or hot tub, or a swimming pool or the like. In addition, the surface may be the surface of a living animal or plant, or may be a wound surface.

The photosensitizer may be applied in a suitable carrier such as water or a solution containing other treatment additives, by spraying, dipping, wiping on, or by other means known to the art. The amount of photosensitizer and energy of photoradiation required for treatment will be readily determined by one of skill in the art without undue experimentation depending on the level of contamination and the material being treated.

This invention also provides a method for treating a fluid or other material as set forth above to inactivate microorganisms which may be present therein comprising adding an inactivation-effective, non-toxic amount of vitamin KS to said fluid or other material. Preferably, but not necessarily, the fluid or other material is irradiated to enhance inactivation of microorganisms. In some cases, using vitamin K5 inactivation occurs in ambient light or in the dark as further discussed in the Examples hereof. Fluids containing red blood cells are preferred for treatment by vitamin K5 in the absence of a photoradiation step. The K5 compound may also coat surfaces such as blood or peritoneal dialysis tubing sets to assure sterile connections and sterile docking.

In decontamination systems of this invention, the photoradiation source may be connected to the photopermeable container for the fluid by means of a light guide such as a light channel or fiber optic tube which prevents scattering of the light between the source and the container for the fluid, and more importantly, prevents substantial heating of the fluid within the container. Direct exposure to the light source may raise temperatures as much as 10 to 15° C., especially when the amount of fluid exposed to the light is small, which can cause denaturization of blood components. Use of the light guide keeps any heating to less than about 2° C. The method may also include the use of temperature sensors and cooling mechanisms where necessary to keep the temperature below temperatures at which desired proteins in the fluid are damaged. Preferably, the temperature is kept between about 0° C. and about 45° C., more preferably between about 4° C. and about 37° C., and most preferably about 22° C.

This invention also provides a system for treating a fluid to inactivate microorganisms which may be present therein comprising:

(a) a container comprising said fluid and an endogenous photosensitizer or endogenously-based photosensitizer derivative, said container being equipped with input means, and having a photopermeable surface sufficient to allow exposure of the fluid therein to an amount of photoradiation sufficient to activate the photosensitizer;

(b) at least one photoradiation source for providing sufficient photoradiation to the fluid in said container of a type and amount selected to activate the photosensitizer whereby microorganisms present are substantially inactivated.

The photoradiation source may be a source of visible radiation or ultraviolet radiation or both. Preferably both visible and ultraviolet radiation are provided, and more preferably the photoradiation is about half ultraviolet and half visible although other ratios could be used. The photoradiation in both the ultraviolet and visible spectra may be supplied concurrently or sequentially, with the visible portion preferably being supplied first. The photoradiation source may be a simple lamp or may consist of multiple lamps radiating at differing wavelengths. The photoradiation source should be capable of delivering from about 1 to at least about 120 J/cm$^2$. The use of mixed ultraviolet and visible light is especially preferred when the photosensitizer is one which loses its capacity to absorb visible light after a period of exposure, such as 7,8-dimethyl-10-ribityl-isoalloxazine.

Any means for adding the photosensitizer to the fluid to be decontaminated and for placing the fluid in the photopermeable container known to the art may be used, such means typically including flow conduits, ports, reservoirs, valves, and the like.

Preferably, the system includes means such as pumps or adjustable valves for controlling the flow of the photosensitizer into the fluid to be decontaminated so that its concentration may be controlled at effective levels as described above. In one embodiment, photosensitizer is mixed with the anticoagulant feed to a blood apheresis system. For endogenous photosensitizers and derivatives having sugar moieties, the pH of the solution is preferably kept low enough, as is known to the art, to prevent detachment of the sugar moiety. Preferably the photosensitizer is added to the fluid to be decontaminated in a pre-mixed aqueous solution, e.g., in water or storage buffer solution.

The photopermeable container for the flow-through system may be a transparent cuvette made of polycarbonate, glass, quartz, polystyrene, polyvinyl chloride, polyolefin, or other transparent material. The cuvette may be enclosed in a radiation chamber having mirrored walls. A photoradiation enhancer such as a second photoradiation source or reflective surface may be placed adjacent to the cuvette to increase the amount of photoradiation contacting the fluid within the cuvette. The system preferably includes a pump for adjusting the flow rate of the fluid to desired levels to ensure substantial decontamination as described above. The cuvette has a length, coordinated with the flow rate therethrough, sufficient to expose fluid therein to sufficient photoradiation to effect substantial decontamination thereof.

Also preferably the cuvette is spaced apart from the light source a sufficient distance that heating of the fluid in the cuvette does not occur, and light is transmitted from the light source to the cuvette by means of a light guide.

In another embodiment the fluid is placed in a photopermeable container such as a blood bag, e.g. used with the apheresis system described in U.S. Pat. No. 5,653,887, and agitated while exposing to photoradiation. Suitable bags include collection bags as described herein. Collection bags used in the Spectra™ system or Trima™ apheresis system of Cobe Laboratories, Inc. are especially suitable. Shaker tables are known to the art, e.g. as described in U.S. Pat. No. 4,880,788. The bag is equipped with at least one port for adding fluid thereto. In one embodiment the photosensitizer, preferably 7,8-dimethyl-10-ribityl-isoalloxazine, is added to the fluid-filled bag in powder form. The bag is then placed on a shaker table and agitated under photoradiation until substantially all the fluid has been exposed to the photoradiation. Alternatively, the bag may be prepackaged with the powdered photosensitizer contained therein. The fluid to be decontaminated may then be added through the appropriate port.

Decontamination systems as described above may be designed as stand-alone units or may be easily incorporated into existing apparatuses known to the art for separating or treating blood being withdrawn from or administered to a patient. For example, such blood-handling apparatuses include the COBE Spectra™ or TRIMA® apheresis systems, available from Cobe Laboratories, Inc., Lakewood, Colo., or the apparatuses described in U.S. Pat. No. 5,653,887 and U.S. Ser. No. 08/924,519 filed Sep. 5, 1997 (PCT Publication No. WO 99/11305) of Cobe Laboratories, Inc. as well as the apheresis systems of other manufacturers. The decontamination system may be inserted just downstream of the point where blood is withdrawn from a patient or donor, just prior to insertion of blood product into a patient, or at any point before or after separation of blood constituents. The photosensitizer is added to blood components along with anticoagulant in a preferred embodiment, and separate irradiation sources and cuvettes are placed downstream from collection points for platelets, for plasma and for red blood cells. The use of three separate blood decontamination systems is preferred to placement of a single blood decontamination system upstream of the blood separation vessel of an apheresis system because the lower flow rates in the separate component lines allows greater ease of irradiation. In other embodiments, decontamination systems of this invention may be used to process previously collected and stored blood products.

When red blood cells are present in the fluid being treated, as will be appreciated by those skilled in the art, to compensate for absorption of light by the cells, the fluid may be thinned, exposed to higher energies of radiation for longer periods, agitated for longer periods or presented to photoradiation in shallower containers or conduits than necessary for use with other blood components.

The endogenous photosensitizers and endogenously-based derivative photosensitizers disclosed herein can be used in pre-existing blood component decontamination systems as well as in the decontamination system disclosed herein. For example, the endogenous photosensitizers and endogenously-based derivative photosensitizers of this invention can be used in the decontamination systems described in U.S. Pat. Nos. 5,290,221, 5,536,238, 5,290,221 and 5,536,238.

Platelet additive solutions comprising endogenous photosensitizers and endogenously-based derivative photosensitizers as described above are also provided herein. Platelet additive solutions known to the art may be used for this purpose and include those disclosed in U.S. Pat. Nos. 5,908,742; 5,482,828; 5,569,579; 5,236,716; 5,089,146; and 5,459,030. Such platelet additive solutions may contain physiological saline solution, buffer, preferably sodium phosphate, and other components including magnesium chloride and sodium gluconate. The pH of such solutions is preferably between about 7.0 and 7.4. These solutions are useful as carriers for platelet concentrates to allow maintenance of cell quality and metabolism during storage, reduce plasma content and extend storage life. The photosensitizer may be present in such solutions at any desired concentration from about 1 $\mu$M to the solubility of the photosensitizer in the solution, and preferably between about 10 $\mu$M and about 100 $\mu$M, more preferably about 10 $\mu$M. In a preferred embodiment, the platelet additive solution also comprises enhancers as described above. A preferred platelet additive solution comprises sodium acetate, sodium chloride, sodium gluconate, 1.5 mM magnesium chloride, 1 mM sodium phosphate 14 $\mu$M 7,8-dimethyl-10-ribityl-isoalloxazine and preferably also 6 mM ascorbate.

DETAILED DESCRIPTION

The decontamination method of this invention using endogenous photosensitizers and endogenously-based derivative photosensitizers is exemplified herein using 7,8-dimethyl-10-ribityl isoalloxazine as the photosensitizer, however, any photosensitizer may be used which is capable of being activated by photoradiation to cause inactivation of microorganisms. The photosensitizer must be one which does not destroy desired components of the fluid being decontaminated, and also preferably which does not break down as a result of the photoradiation into products which significantly destroy desired components or have significant toxicity. The wavelength at which the photosensitizer is activated is determined as described herein, using literature sources or direct measurement. Its solubility in the fluid to be decontaminated or in a combination of carrier fluid and fluid to be contaminated is also so determined. The ability of photoradiation at the activating wavelength to penetrate the fluid to be decontaminated must also be determined as taught herein. Appropriate temperatures for the reaction of the photosensitizer with its substrate are determined, as well as the ranges of temperature, photoradiation intensity and duration, and photosensitizer concentration which will optimize microbial inactivation and minimize damage to desired proteins and/or cellular components in the fluid. Examples 1–7 and FIGS. 1–5 illustrate the determination of information required to develop a flow-through decontamination system of this invention.

Figure 6:
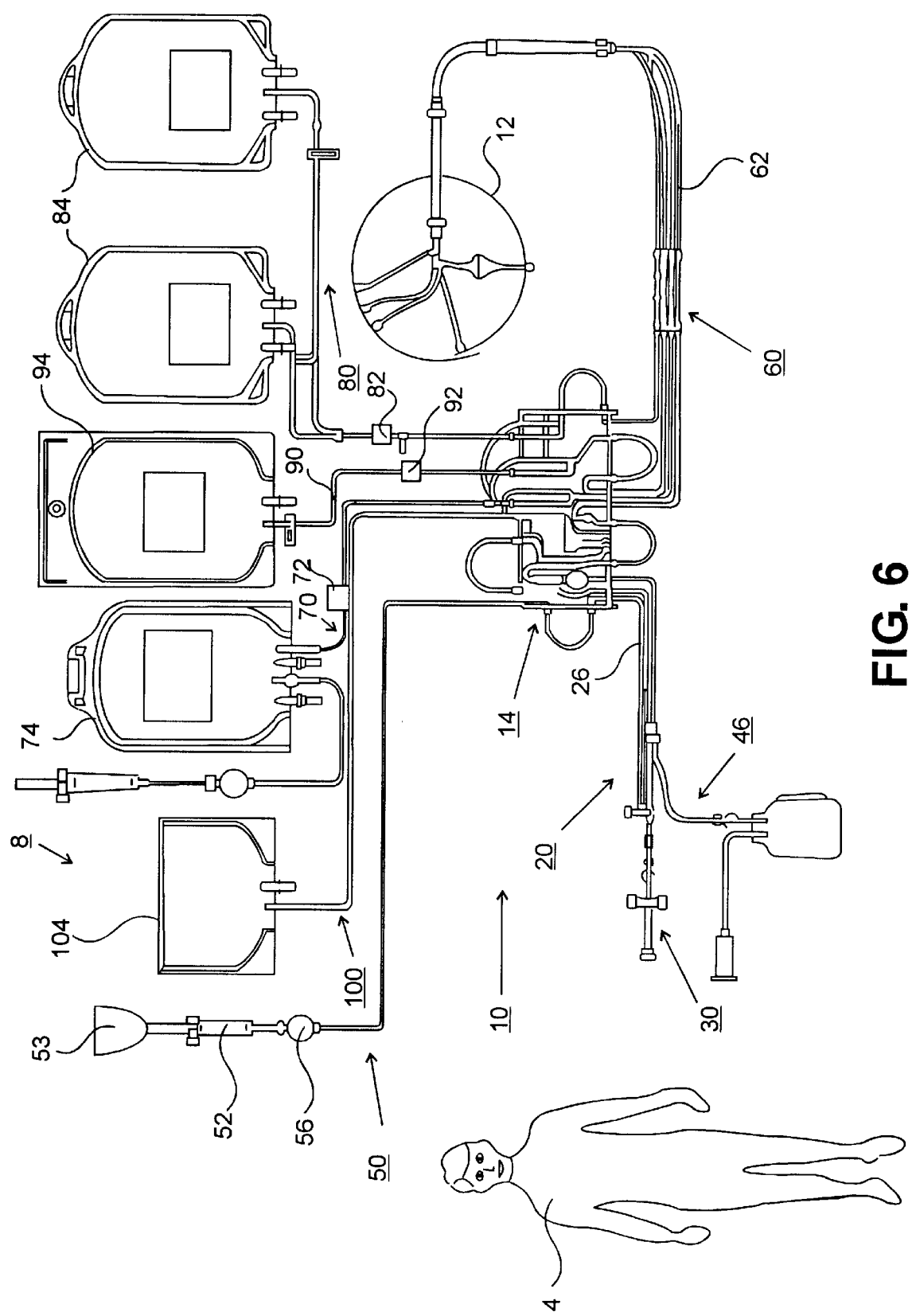
FIG. 6 depicts a blood separation apparatus incorporating the photoradiation device of this invention.
Figure 7:
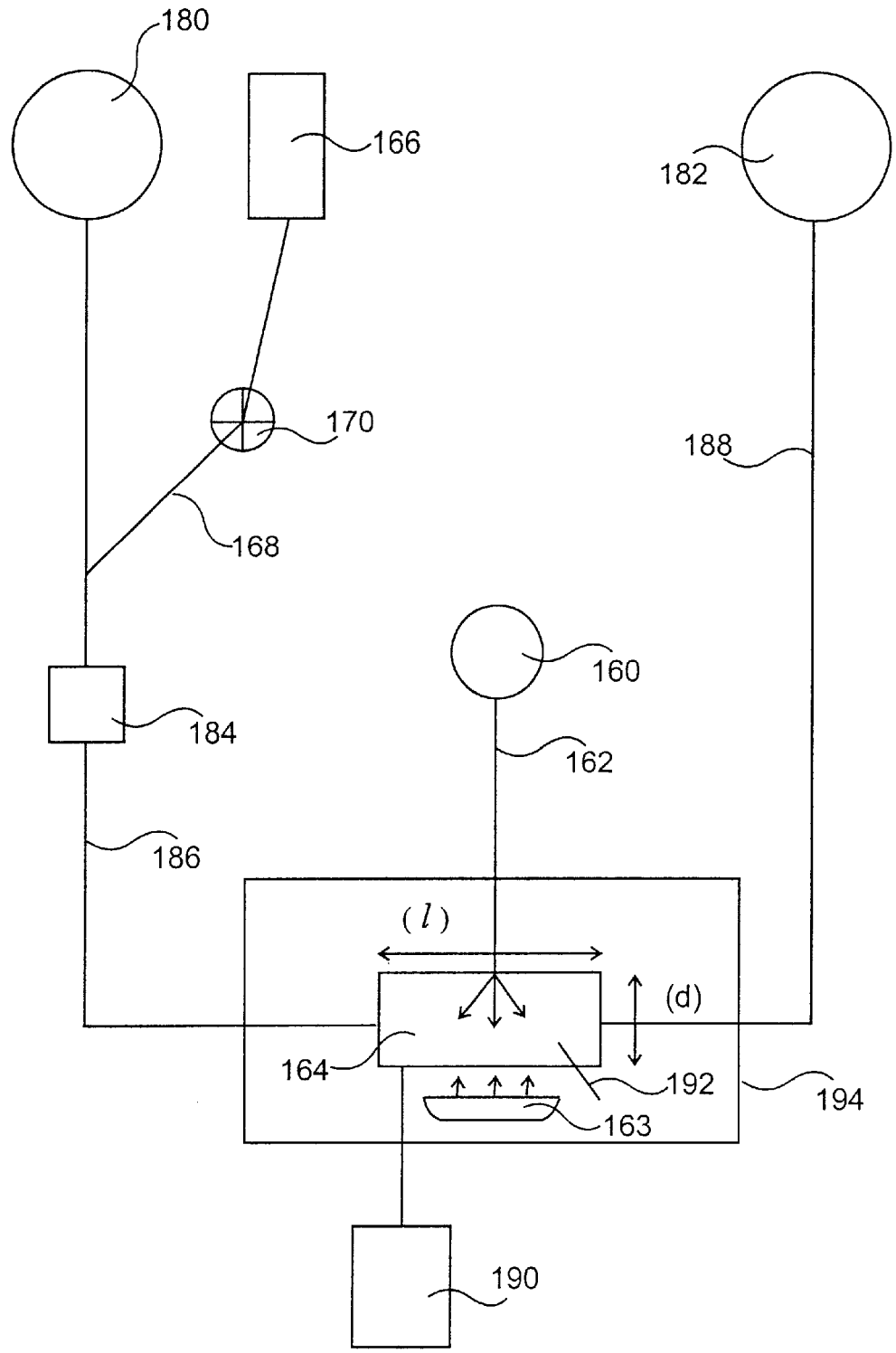
FIG. 7 depicts the decontamination assembly of this invention.
Figure 8:
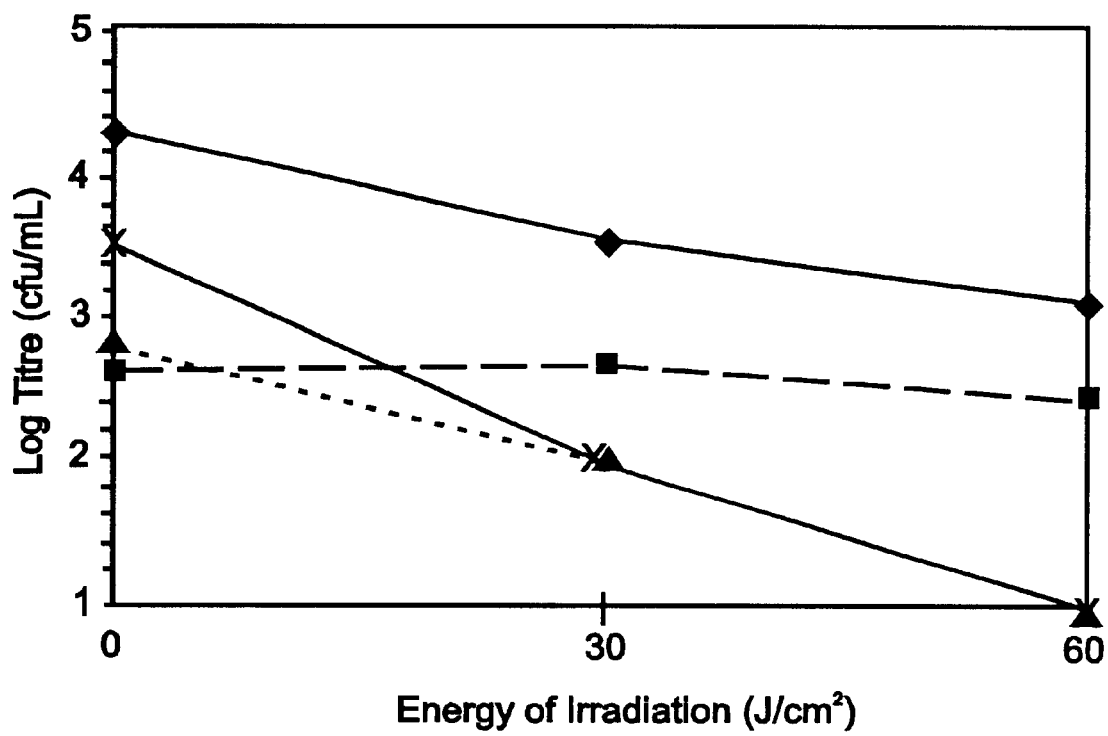
FIG. 8 depicts inactivation of bacteria in platelet preparations using vitamin K5 as the photosensitizer as a function of energy of irradiation.
Figure 9:
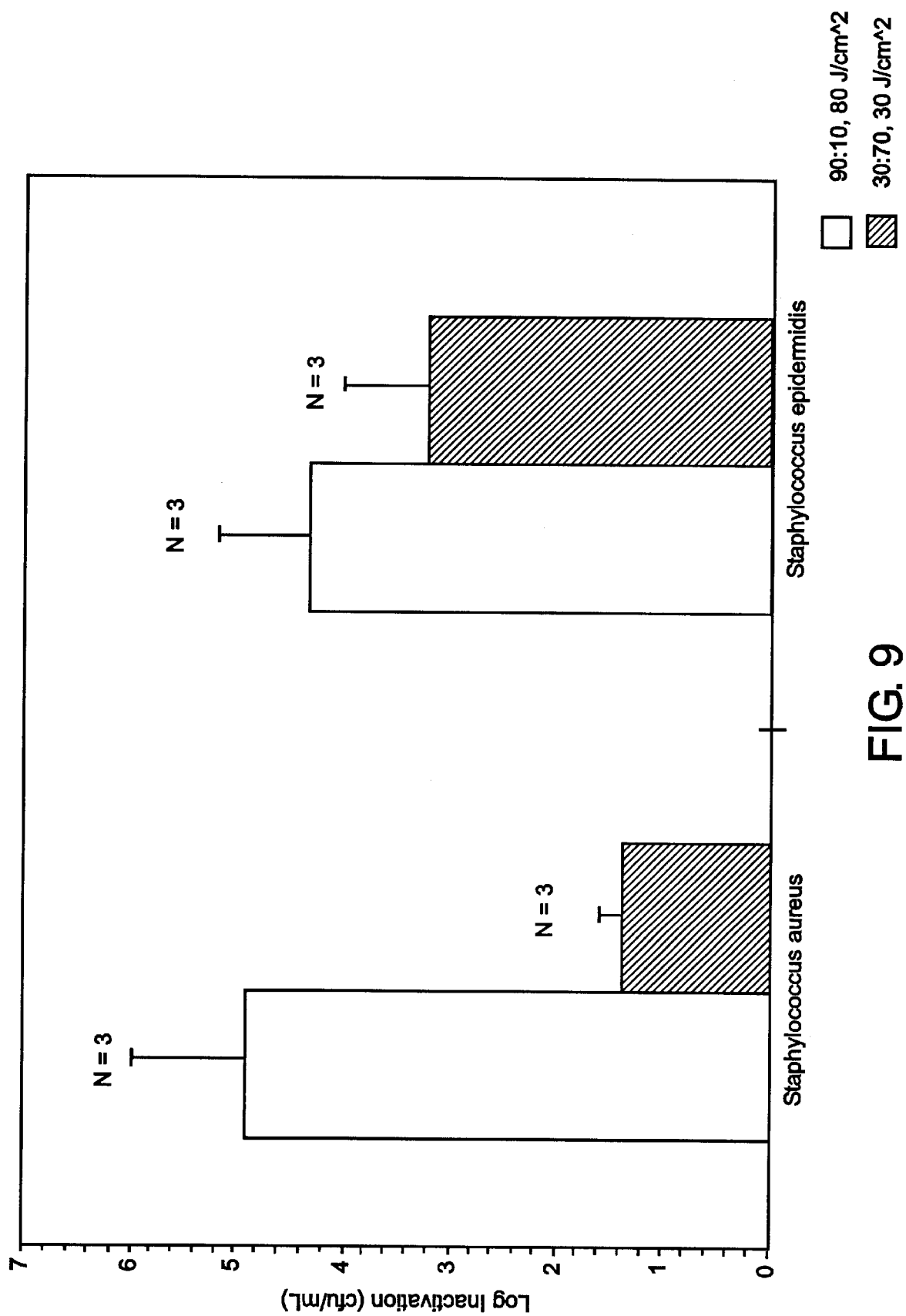
FIG. 9 depicts inactivation of bacteria as a function of platelet preparation and energy of irradiation, using 90% platelets and 10% platelet additive solution (90:10) and 30% platelets with 70% additive solution (30:70).

Once such system requirements have been determined for flow-through systems, apparatuses may be designed which provide the correct flow rates, photopermeabilities, and light intensities to cause inactivation of microorganisms present in the fluid, as is taught herein. The fluid to be decontaminated is mixed with photosensitizer and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, which may be increased through the use of light guides to carry the photoradiation directly to the container for the fluid, an appropriate photopermeable material for the container for the fluid, an appropriate depth to allow full penetration of the photoradiation into the container, photoradiation enhancers such as one or more additional photoradiation sources, preferably on the opposite side of the container from the first, or reflectors to reflect light from the radiation source back into the container, appropriate flow rates for the fluid in the container and an appropriate container length to allow sufficient time for inactivation of microorganisms present. Temperature monitors and controllers may also be required to keep the fluid at optimal temperature. FIG. 6 depicts a decontamination system of this invention as part of an apparatus for separating blood components, and FIG. 7 provides details of a preferred decontamination system.

For batch systems, it is preferred to place the fluid to be decontaminated along with photosensitizer in bags which are photopermeable or at least sufficiently photopermeable to allow sufficient radiation to reach their contents to activate the photosensitizer. Sufficient photosensitizer is added to each bag to provide inactivation, preferably to provide a photosensitizer concentration of at least about 10 $\mu$M, and the bag is agitated while irradiating, preferably at about 1 to about 120 J/cm$^2$ for a period of between about 6 and about 36 minutes to ensure exposure of substantially all the fluid to radiation. Preferably, a combination of visible light and ultraviolet light is used concurrently. The photosensitizer may be added in powdered form.

The method preferably uses endogenous photosensitizers, including endogenous photosensitizers which function by interfering with nucleic acid replication. 7,8-dimethyl-10-ribityl isoalloxazine is the preferred photosensitizer for use in this invention. The chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). Cadet et al. (1983) J. Chem., 23:420–429, clearly demonstrate the effects of 7,8-dimethyl-10-ribityl isoalloxazine are due to non-singlet oxygen oxidation of guanosine residues. In addition, adenosine bases appear to be sensitive to the effects of 7,8-dimethyl-10-ribityl isoalloxazine plus UV light. This is important since adenosine residues are relatively insensitive to singlet oxygen-dependent processes. 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species. Since indiscriminate damage to cells and proteins arises primarily from singlet oxygen sources, this mechanistic pathway for the action of 7,8-dimethyl-10-ribityl isoalloxazine allows greater selectivity in its action than is the case with compounds such as psoralens which possess significant Type II chemistry.

FIG. 6 shows a blood apparatus device and apheresis system incorporating the photoradiation devices of this invention. Whole blood is withdrawn from a donor/patient 4 and is provided to an apheresis system or blood component separation device 8 where the blood is separated into the various component types and at least one of these blood component types is removed from the device 8. These blood components may then be provided for subsequent use by another or may undergo a therapeutic treatment and be returned to the donor/patient 4.

In the blood component separation device 8, blood is withdrawn from the donor/patient 4 and directed through an extracorporeal tubing circuit 10 and a blood-processing vessel 12, defining a completely closed and sterile system. The blood component separation device 8 is connected to a pump (not shown). Blood flows from the donor/patient 4 through the extracorporeal tubing circuit 10 and into rotating blood processing vessel 12. The blood within the blood processing vessel 12 is separated into various blood component types, and these component types (platelets, plasma, red blood cells) are continually removed from the blood processing vessel 12. Blood components which are not being retained for collection or for therapeutic treatment (e.g., red blood cells, white blood cells, plasma) are also removed from the blood processing vessel 12 and returned to the donor/patient 4 via the extracorporeal tubing circuit 10.

Operation of the blood component separation device is preferably controlled by one or more computer processors included therein.

Extracorporeal tubing circuit 10 comprises a cassette assembly 14 and a number of tubing assemblies 20, 50, 60, 80, 90, 100 interconnected therewith. Blood removal/return tubing assembly 20 provides a single needle interface between a donor/patient 4 and cassette assembly 14, and blood inlet/blood component tubing subassembly 60 provides the interface between cassette assembly 14 and blood processing vessel 12. An anticoagulant tubing assembly 50, platelet collection tubing assembly 80, plasma collection tubing assembly 90, red blood cell collection tubing assembly 70 and vent bag tubing subassembly 100 are also interconnected with cassette assembly 14.

The blood removal/return tubing assembly 20 includes a needle subassembly 30 interconnected therewith and anticoagulant tubing 26 connecting to anticoagulant tubing assembly 50 through cassette assembly 14.

Cassette assembly 14 includes front and back molded plastic plates that are hot-welded together to define a rectangular cassette member having integral fluid passageways. The cassette assembly 14 further includes a number of outwardly extending tubing loops interconnecting various integral passageways. The integral passageways are also interconnected to the various tubing assemblies.

Specifically, cassette assembly 14 interconnects with anticoagulant tubing 26 of the blood removal/return tubing assembly 20 and with anticoagulant tubing assembly 50. The anticoagulant tubing assembly 50 includes a spike drip chamber 52 connectable to anticoagulant and photosensitizer source 53 and a sterilizing filter 56. During use, the anticoagulant tubing assembly 50 supplies anticoagulant mixed with photosensitizer to the blood removed from donor/patient 4 to reduce or prevent any clotting in the extracorporeal tubing circuit 10. Many anticoagulants are known to the art, e.g. as disclosed in Chapter 3 of the AABB Technical Manual, 11th edition, 1993, including ACD-A, CPD, CP2D, CPDA-1 and heparin. These as well as cell storage solutions, AS-1, AS-3 and AS-5, are all compatible with the endogenous photosensitizers and endogenously-based derivative photosensitizers described herein.

Cassette assembly 14 also includes an interconnection with blood removal tubing of the blood removal/return tubing assembly 20. Blood passes through pressure sensors, and an inlet filter in cassette assembly 14 and thence to blood inlet tubing 62. Blood inlet tubing 62 is also interconnected with blood processing vessel 12 to provide whole blood thereto for processing.

To return separated blood components to cassette assembly 14, the blood inlet/blood component tubing assembly 60 further includes red blood cell (RBC)/plasma outlet tubing, platelet outlet tubing and plasma outlet tubing interconnected with corresponding outlet ports on blood processing vessel 12. The red blood cell (RBC)/plasma outlet tubing channels the separated red blood cell (RBC)/plasma component through cassette assembly 14 to red blood cell collection tubing assembly 70 through first decontamination system 72. The platelet outlet tubing channels separated platelets through cassette assembly 14 to platelet collection tubing assembly 80 through second decontamination system 82. The plasma outlet tubing channels separated plasma through cassette assembly 14 to plasma collection tubing assembly 90 through third decontamination system 92. After irradiation in the decontamination systems 72, 82 and 92, to activate the photosensitizer and inactivate microorganisms present, the blood components are collected in red blood cell collection bag 74, platelet collection bags 84, and plasma collection bag 94. Vent bag 104 may be used to vent gases within the system.

FIG. 7 depicts a stand-alone version of the decontamination assembly of this invention. Blood product 180 (which may be recently collected blood or blood component or stored blood) is connected to blood product line 186 which leads through pump 184 to decontamination cuvette 164. Photosensitizer reservoir 166 is connected to photosensitizer input line 168 equipped with input pump 170, and leads into blood product line 186 upstream from decontamination cuvette 164. Decontamination cuvette 164 is a photopermeable cuvette of a depth (d) and a length (l) selected to ensure decontamination. Cooling system 190 combined with temperature monitor 192 are connected with decontamination cuvette 164 for controlling the temperature of the fluid. Decontamination cuvette 164 is connected via light guide 162 to photoradiation source 160. A photoradiation enhancer 163 is placed adjacent to (either touching or spaced apart from) decontamination cuvette 164 to increase the amount of photoradiation reaching the blood product in the cuvette. Decontaminated blood product line 188 leads from decontamination cuvette 164 to decontaminated blood product collection 182.

In operation, blood product 180 is conducted into blood product line 186 where it is joined by photosensitizer from photosensitizer reservoir 166 flowing at a rate controlled by photosensitizer input pump 170 in photosensitizer input line 68 which joins blood product line 186. The flow rate in blood product line 186 is controlled by pump 184 to a rate selected to ensure decontamination in decontamination cuvette 164. Temperature monitor 192 measures the temperature of fluid in cuvette 164 and controls cooling system 190 which keeps the temperature in the cuvette within a range required for optimal operation. The blood product in decontamination cuvette 164 is irradiated by photoradiation from photoradiation source 160 conducted in light guide 162. The photoradiation source may comprise two or more actual lights. The arrows indicate photoradiation from the end of light guide 162 propagating in the blood product inside transparent decontamination cuvette 164. Adjacent to decontamination cuvette 164 is photoradiation enhancer 163 which may be an additional source of photoradiation or a reflective surface. The arrows from photoradiation enhancer 163 pointing toward decontamination cuvette 164 indicate photoradiation from photoradiation enhancer 163 shining on the blood product material in cuvette 164. Decontaminated blood product exits decontamination cuvette 164 via decontaminated blood product line 188 and is collected at decontaminated blood product collection 182.

In one embodiment using 7,8-dimethyl-10-ribityl isoalloxazine from Sigma Chemical Company as the photosensitizer, a light guide from EFOS Corporation, Williamsville, N.Y. composed of optical fibers is used. The system is capable of delivering a focused light beam with an intensity of 6,200 mW/cm$^2$ in the region of 355–380 nm. It is also possible to use interchangeable filters with the system to achieve outputs of 4,700 mW/cm$^2$ in the spectral region of 400–500 nm. In both cases, the output of light in the region of 320 nm and lower is negligible. Light guides of varying dimensions (3, 5 and 8 mm) are available with this system. The light exits the light guide tip with a 21 degree spread. The 8 mm light guide is appropriate, correctly placed, to adequately illuminate the face of the preferred decontamination cuvette which is a standard cuvette used on Cobe Spectra® disposables sets from Industrial Plastics, Inc., Forest Grove, Oreg.

The flow rate is variable and is determined by the amount of light energy intended to be delivered to the sample. The flow rate is controlled by means of a peristaltic pump from the Cole-Parmer Instrument Company, Vernon Hills, Ill. Flow rates and type of input stream may be controlled via a computer processor as is known to the art.

Figure 23:
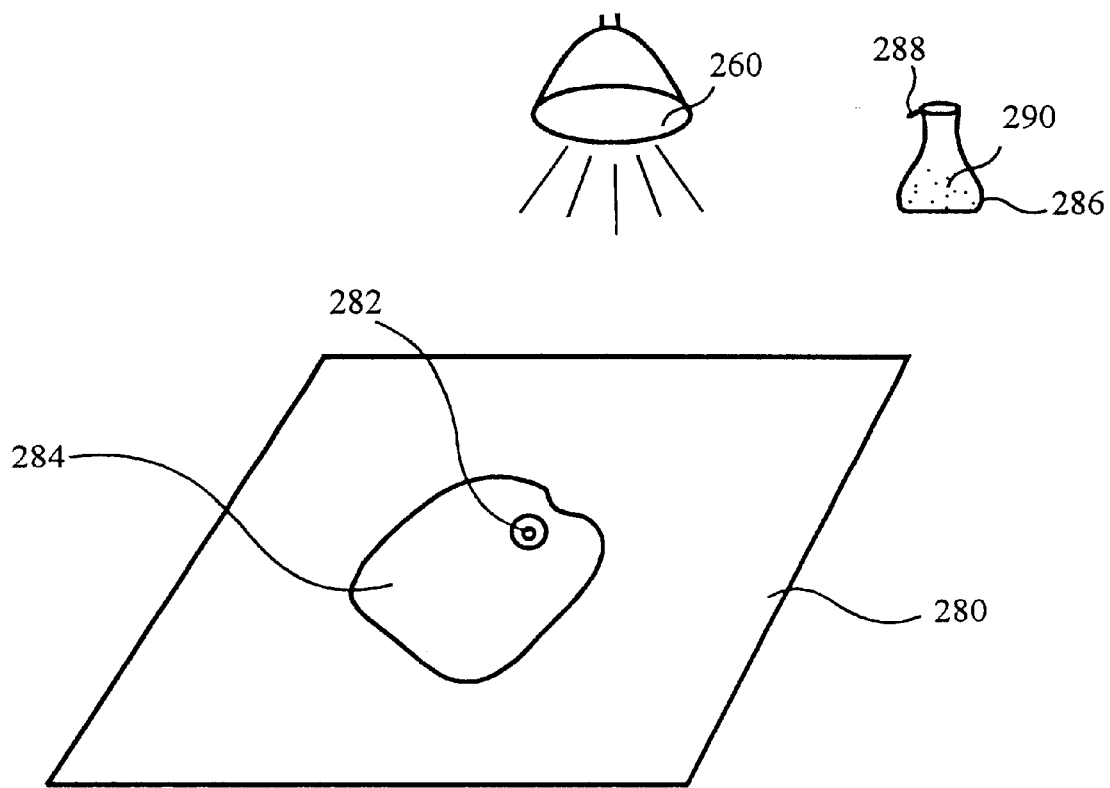
FIG. 23 shows an embodiment of this invention using a blood bag to contain the fluid being treated and photosensitizer and a shaker table to agitate the fluid while exposing to photoradiation from a light source.

FIG. 23 depicts an embodiment of this invention in which fluid to be decontaminated is placed in a blood bag 284 equipped with an inlet port 282, through which photosensitizer in powder form 284 is added from flask 286 via pour spout 288. Shaker table 280 is activated to agitate the bag 284 to dissolve photosensitizer 290 while photoradiation source 260 is activated to irradiate the fluid and photosensitizer in bag 284. Alternatively, the bag can be provided prepackaged to contain photosensitizer and the fluid is thereafter added to the bag.

The methods of this invention do not require the use of enhancers such as "quenchers" or oxygen scavengers, however these may be used to enhance the process by reducing the extent of non-specific cell or protein-damaging chemistry or enhancing the rate of pathogen inactivation. Further preferred methods using non-toxic endogenous photosensitizers and endogenously-based derivative photosensitizers do not require removal of photosensitizers from the fluid after photoradiation. Test results show little or no damage to other blood components, e.g. platelets remain biologically active five days post-treatment.

EXAMPLES

Example 1

Absorbance Profile of 7,8-dimethyl-10-ribityl isoalloxazine

Figure 1:
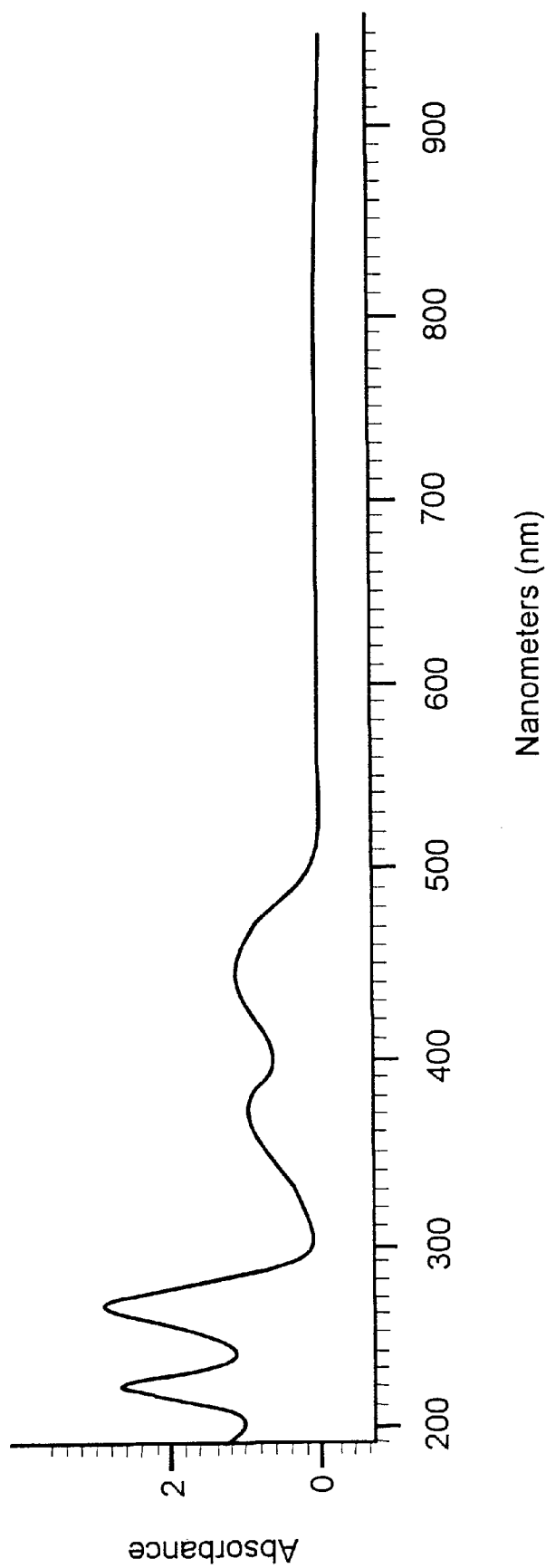
FIG. 1 depicts the riboflavin absorbance spectrum.

A sample of 7,8-dimethyl-10-ribityl isoalloxazine (98% purity) was obtained from Sigma Chemical Company. A portion of this sample was submitted for analysis using a scanning UV spectrophotometer. The range studied covered the region of 200 to 900 nm. For analysis, the sample was dissolved in distilled water. A sample spectrum from this analysis is shown in FIG. 1.

Results were consistent with those reported in the literature for the absorbance maxima and extinction coefficients for 7,8-dimethyl-10-ribityl isoalloxazine

| Literature λmax (ε) | Measured λmax (ε) |
|---|---|
| 267 (32,359) | 222 (30,965) |
| | 265 (33,159) |
| 373 (10,471) | 373 (10,568) |
| 447 (12,303) | 445 (12,466) |

Appropriate wavelengths for irradiation are 373 and 445 nm. The extinction coefficients observed at these absorbance maxima is sufficient to ensure adequate activation of the sensitizer in solution.

Example 2

Solubility of 7,8-dimethyl-10-ribityl isoalloxazine
Solubility in Isolyte S, pH 7.4 Media
The maximum solubility of 7,8-dimethyl-10-ribityl isoalloxazine in Isolyte S media was determined as follows:

7,8-dimethyl-10-ribityl isoalloxazine was mixed with Isolyte S until a precipitate was formed. The mixture was agitated at room temperature for one hour and vortex mixed to ensure complete dissolution of the suspended material. Additional 7,8-dimethyl-10-ribityl isoalloxazine was added until a solid suspension remained despite additional vortex mixing. This suspension was then centrifuged to remove undissolved material. The supernatant from this preparation was removed and analyzed using a spectrophotometer. The absorbance values of the solution were determined at 447 nm and 373 nm. From the extinction coefficients that were determined previously, it was possible to estimate the concentration of the saturated solution Concentration (373)=110 μM=42 μg/mL
Concentration (447)=109 μM=40.9 μg/mL
Solubility in ACD-A Anticoagulant
The same procedure described above was repeated using ACD-A Anticoagulant. The values obtained from these measurements were as follows:

Concentration (373)=166 μM=63 μg/mL
Concentration (447)=160 μM=60.3 μg/mL
The values obtained from these studies indicate an upper limit of solubility of the compound that may be expected.

Example 3

Photodecomposition of 7,8-dimethyl-10-ribityl isoalloxazine in Aqueous Media

Figure 3:
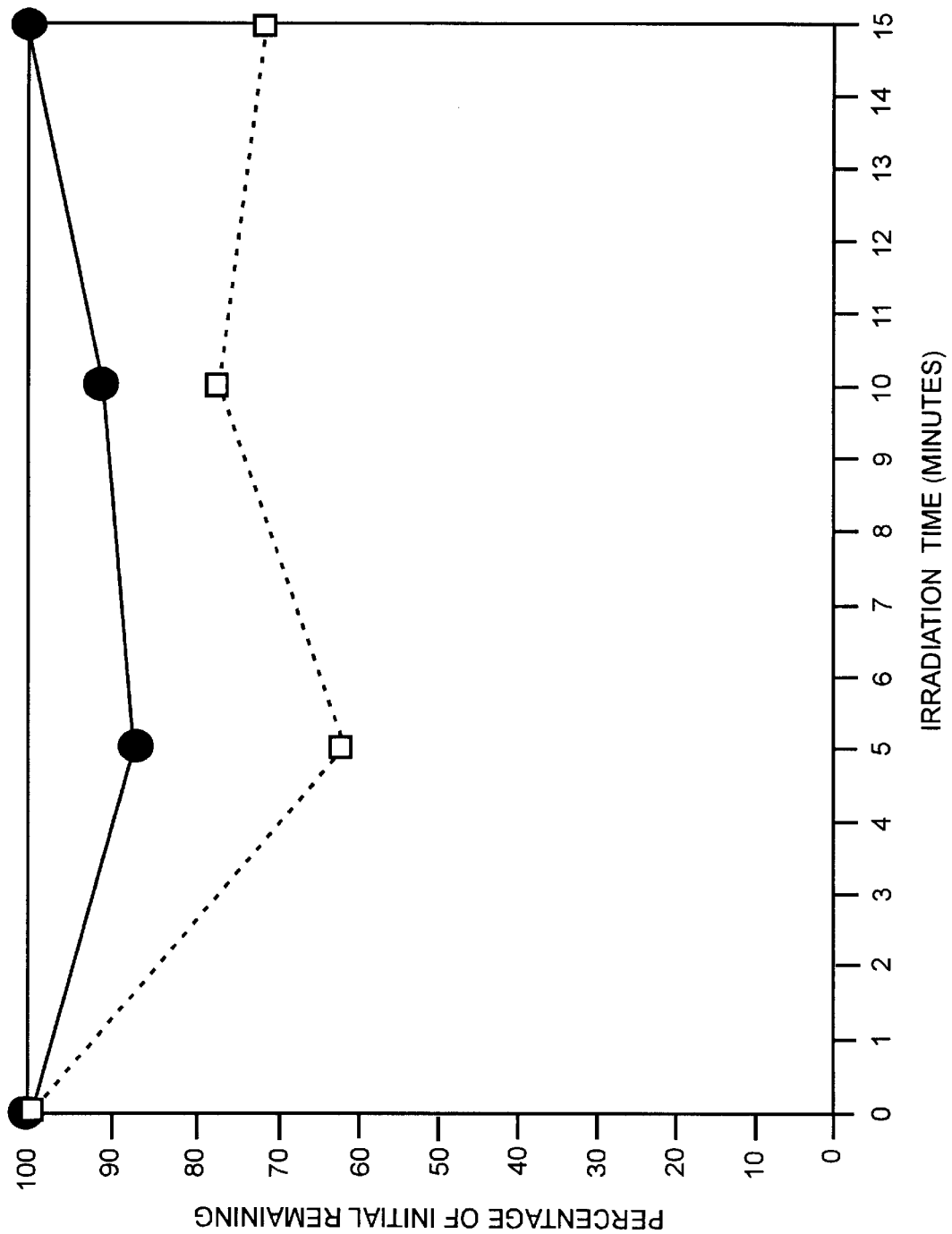
FIG. 3 depicts photodecomposition over time of riboflavin in anticoagulant Acid Citrate Dextrose (ACD) solution. The solid line with circles indicates percent of initial riboflavin remaining at 373 nm. The dotted line with squares indicates percent of initial riboflavin remaining at 447 nm.

A solution of 7,8-dimethyl-10-ribityl isoalloxazine in Sigma ACD-A was prepared at a concentration of 63 μg/mL. This preparation was taken up into a glass pipette and placed in the path of a UV light source (365 nm λmax with filters to remove light below 320 nm). The suspension was irradiated for specific intervals at which aliquots were removed for spectroscopic analysis. The absorbance of the dissolved 7,8-dimethyl-10-ribityl isoalloxazine was monitored at 373 and 447 nm at each time interval. The results are depicted in FIG. 3 and Table 1.

TABLE 1

Photodecomposition of 7,8-dimethyl-10-ribityl isoalloxazine
Upon Exposure to UV Light (365 nm) in Acid Solution

| Irradiation Time | % of Initial, 373 nm | % of Initial, 447 nm |
|---|---|---|
| 0 | 100 | 100 |
| 5 | 87.3 | 61.6 |
| 10 | 90.5 | 76.6 |
| 15 | 100 | 70 |

The absorption profile for the solution at 373 nm indicates that no significant decomposition of the reagent occurred over the entire irradiation period. The absorbance of light at this wavelength corresponds to n-π* electronic transitions. The absence of a decrease in the intensity of this peak over time indicates that the ring structure of the molecule is intact despite prolonged irradiation under these conditions. The absorbance of the molecule at 447 nm is due to π-π* electronic state transitions. The decrease in the absorbance of the molecule at this wavelength with increasing irradiation times is indicative of subtle alterations in the resonance structure of the molecule. This change is most likely due to the loss of ribose from the ring structure of the 7,8-dimethyl isoalloxazine backbone and the formation of 7,8-dimethylalloxozine as a result. These changes are consistent with literature reports on the behavior of the molecule upon irradiation with UV light.

The apparent lack of decomposition of the ring structure of the molecule is in stark contrast to observations with psoralen based compounds under similar conditions. During irradiation, a significant fluorescence of the molecule in solution was observed. This behavior of the molecule is consistent with the resonance features of the ring structure and provides a means for the dissipation of energy in the excited state molecule in a non-destructive fashion.

Example 4

Flow System Concept Evaluation
Light Transmission Properties of Existing Spectra Cuvette
The existing Spectra Cuvette is composed of polycarbonate. The light transmission properties of this cuvette were measured at 373 and 447 nm by placing the cuvette in the light path of a UV spectrophotometer. The values obtained were as follows:

| Wavelength of Light | % Transmittance |
|---|---|
| 373 nm | 66% |
| 447 nm | 80% |

Figure 4:
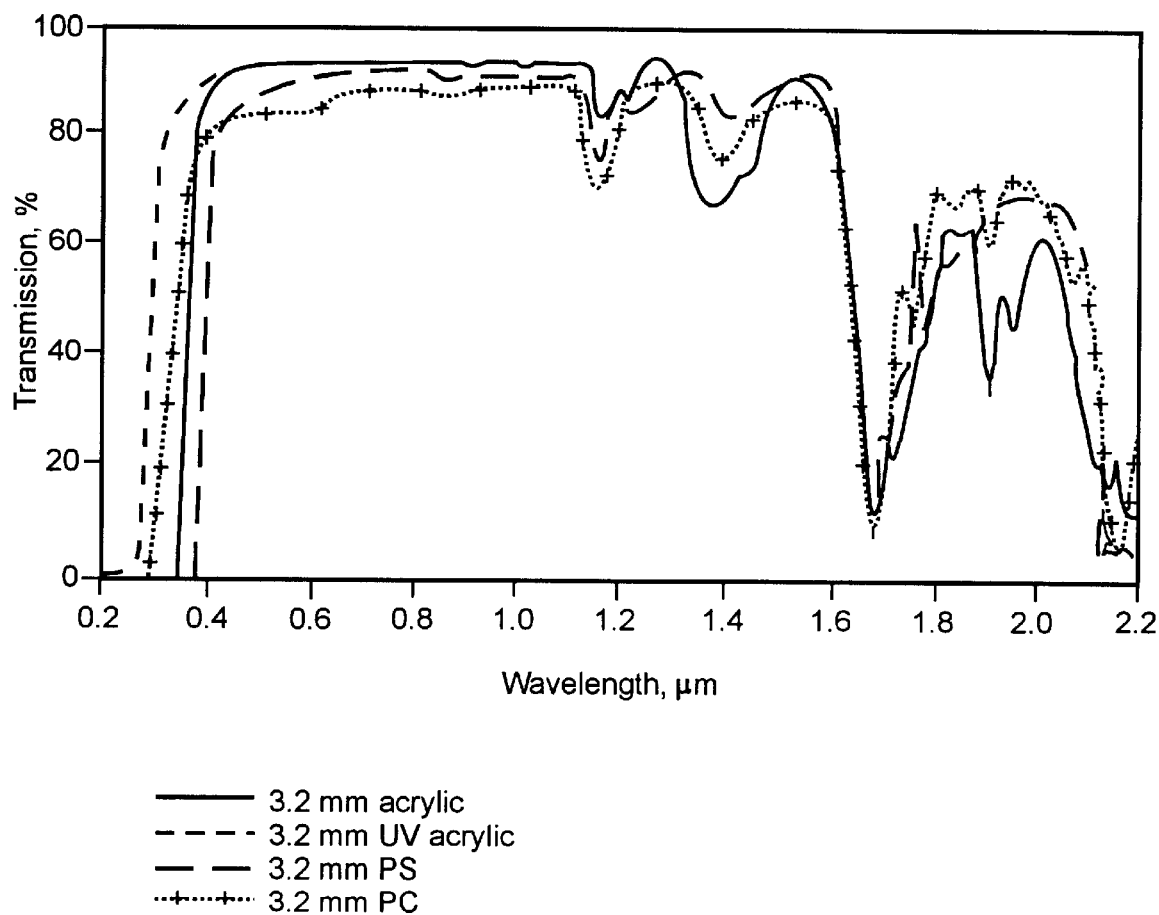
FIG. 4 depicts the transmission profile of various plastic cuvettes as a function of wavelength. The solid line represent a 3.2 mm acrylic cuvette. The dotted line (----) represents a 3.2 mm UV acrylic cuvette. The dashed line (——) represents a 3.2 mm polystyrene (PS) cuvette, and the crossed line indicates a 3.2 mm polycarbonate (PC) cuvette.
Figure 5:
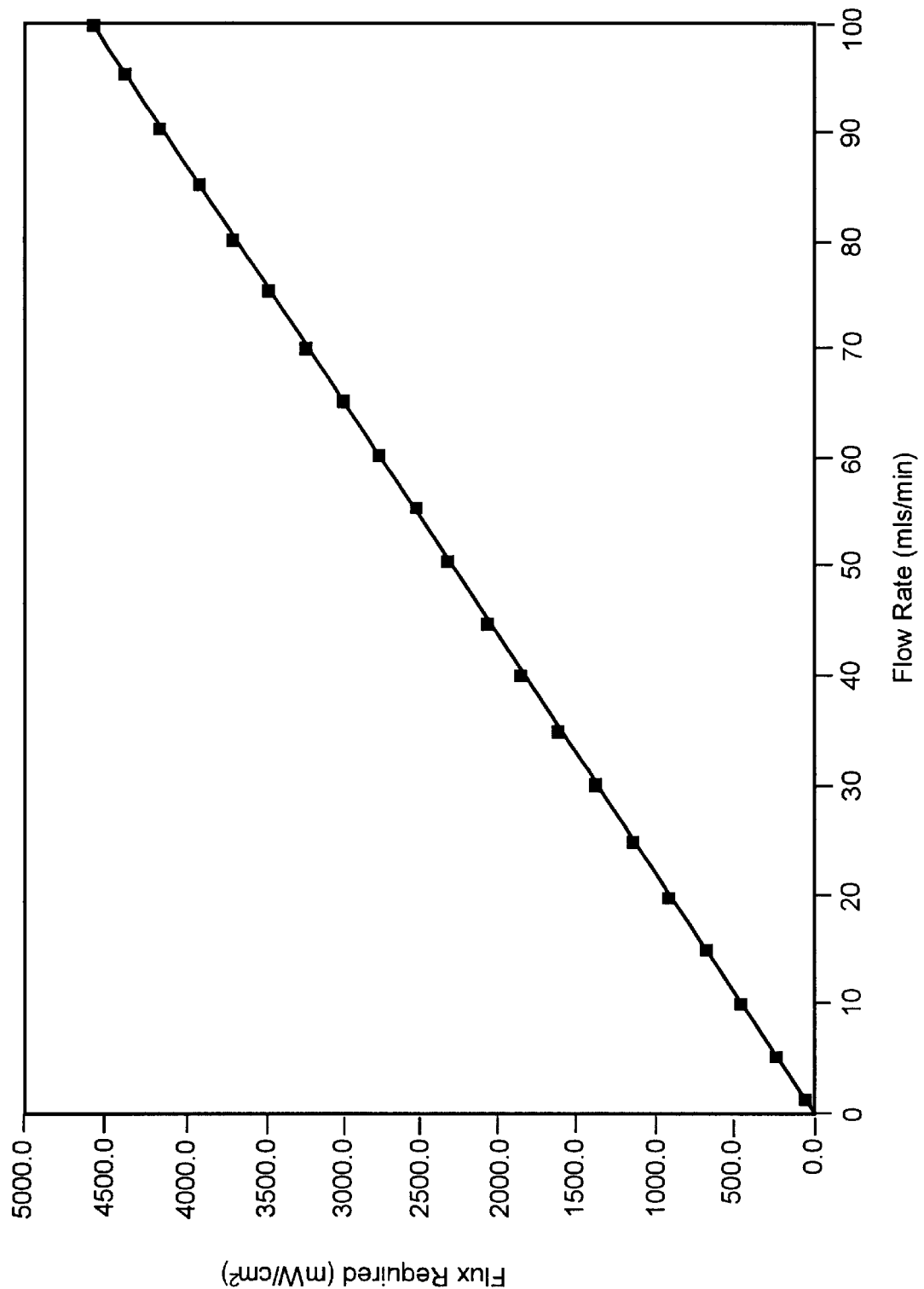
FIG. 5 depicts the light flux required in mW per cm$^2$ as a function of flow rate, i.e. the flux required to deliver one joule/cm$^2$ to a sample in the cuvette.

These results are consistent with those reported in the literature for polycarbonate plastics (see FIG. 4). The literature values indicate a steep shoulder for the transmission of light through polycarbonates in the region of 300 nm. For the region above 350 nm, the light transmission properties are adequate for this application.
Light Flux Requirements Calculated as a Function of Flow Rates
In order for a flow system to be feasible, the sample must be provided with an adequate flux of light during its presence in the beam path. If the proposed Spectra cuvette were to serve this purpose, then it is possible to estimate the light flux requirements as a function of flow rates through the cuvette as follows: The volume of solution present in the irradiation zone of the cuvette is ca. 0.375 mls. The transit time for a cell in this region of the cuvette can be determined from the following equation:

$$T = \frac{\text{Volume of Cuvette (mls)}}{\text{Flow Rate (mls/min)}}$$

At 100 mls per minute, the transit time (T) would be 0.00375 min=0.225 seconds.

The energy to which a sample is exposed is dependent on the flux according to the following equation:

$$\text{Energy } (E, \text{Joules/cm}^2) = \frac{\text{Flux } (\phi, \text{mW/cm}^2) * \text{Time}(T, \text{sec.})}{1000}$$

If we assume that 1 Joule/cm² is required to activate the sensitizer adequately and the transit time (T) is 0.22 seconds (i.e., flow rate of 100 mls/min through the cuvette), then the required Flux during the sample's transit through the cuvette is 4,545 mW/cm². A graph depicting the relationship of the required flux from the light source to flow rates through the cuvette is provided in FIG. 5.

These results indicate that, for a flow system to operate properly, UV sources with outputs in the region of Watts/cm² are required.

Figure 2:
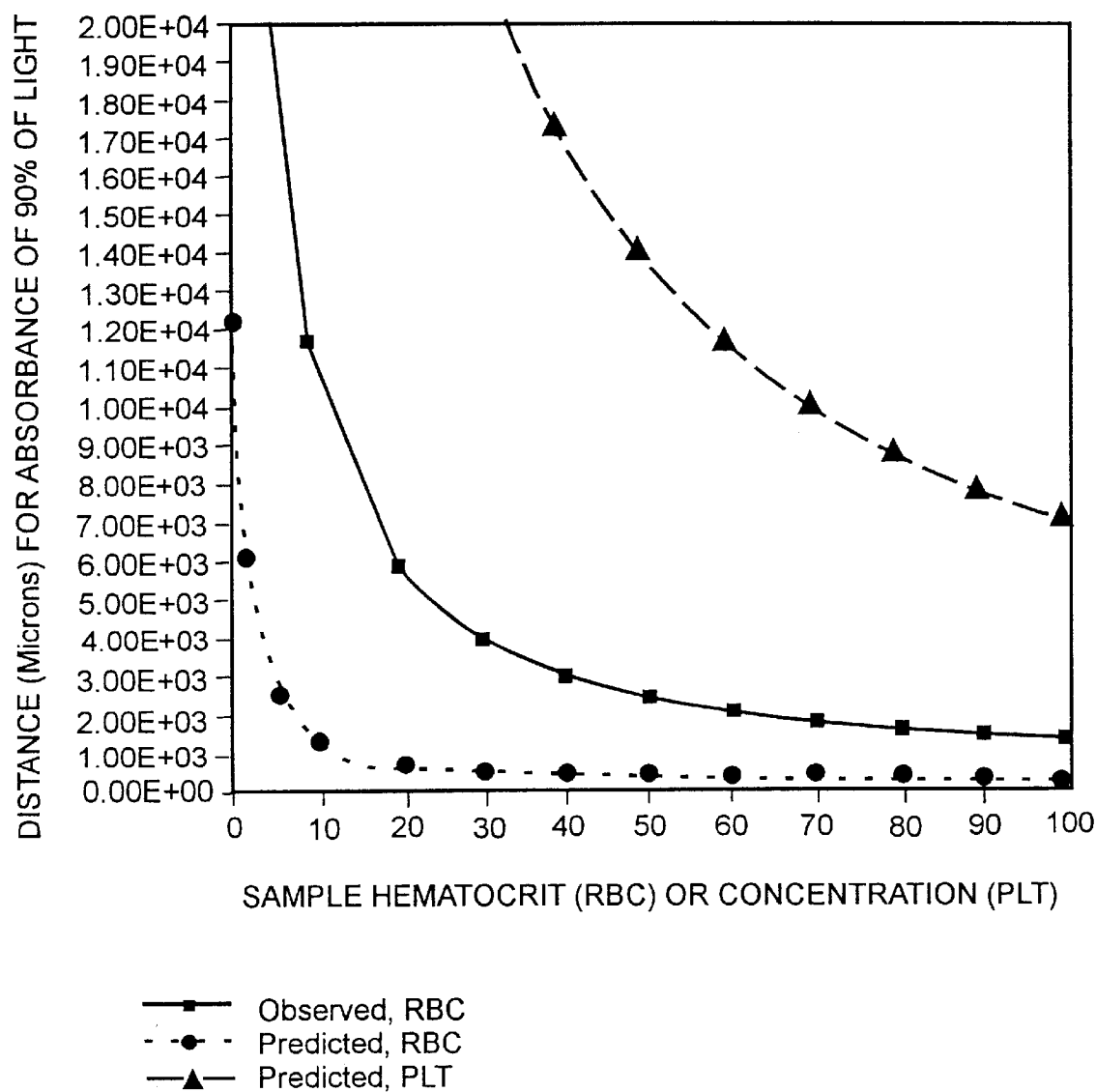
FIG. 2 depicts a correlation of light absorbance and hematocrit observed and predicted for red blood cells, and predicted for platelets.

FIG. 2 shows how absorbance should vary with concentration of platelets.

Example 5

Absorbance of Red Blood Cells

In order to evaluate the extent to which UV light can penetrate a red cell sample and the effects of sample thickness and hematocrit on the extent of light penetration, several preliminary experiments were carried out using chemical actinometry, a method for determining the actual amount of light intensity emanating from a source by measuring the ability and extent to which absorbed light can effect a chemical reaction. For these studies, a ferrioxalate solution was utilized in order to measure the source intensity relative to that observed for water. Details of the chemical reaction and the methods utilized for sample preparation are as taught in Gordon, A. J. and Ford, R. A. (1972), "The Chemist's Companion: A Handbook of Practical Data, Techniques and References" (John Wiley & Sons), pp. 362–368.

Samples of iron (III) oxalate were prepared in the test material (water or blood product at varying red cell hematocrits) at a concentration of 0.15 M. These samples were then loaded into a standard Spectra cuvette and placed in the irradiation assembly. Samples were exposed for predetermined time intervals corresponding to the desired energy dose level (1 J/cm²). The samples were then removed and the amount of conversion of $Fe^{3+}$ to $Fe^{2+}$ was determined by reading the absorbance of the test article in a 1,10-phenanthroline solution at 510 nm as described in Gordon, A. J. and Ford, R. A., supra. Higher absorbance values are indicative of greater light penetration into the sample. The absorbance value observed for water after exposure to 1 J/cm² UV radiation was used as the 100% Transmittance level. All values for red cell samples were determined relative to this standard.

TABLE 2

Absorbance Readings After Exposure of Samples to 1 J/cm² UVA Light. All Average Values Represent the Mean of 6 Experiments. % Transmittance Values Are Calculated Relative to Water Samples.

| Absorbance at 510 nm | Average | Standard Deviation | % Transmittance | Standard Deviation |
|---|---|---|---|---|
| Water | 2.40 | 0.04 | 100 | 0.0 |
| RBC, 1.3% Hematocrit | 2.40 | 0.10 | 99.5 | 4.8 |
| RBC, 3.7% Hematocrit | 1.46 | 0.38 | 60.6 | 15.4 |
| RBC, 5.07% Hematocrit | 0.20 | 0.26 | 8.3 | 10.8 |
| RBC, 6.0% Hematocrit | 0.13 | 0.09 | 5.2 | 3.9 |
| RBC, 10.2% Hematocrit | 0.23 | 0.19 | 9.7 | 7.9 |
| RBC, 16.3% Hematocrit | 0.25 | 0.11 | 10.4 | 4.6 |
| RBC, 21.8% Hematocrit | 0.09 | 0.06 | 3.6 | 2.6 |
| RBC, 80.2% Hematocrit | 0.01 | 0.11 | 0.3 | 4.4 |

Using these values, it is possible to calculate the penetration depth of UV light by using Beer's Law (A=ε b C).

From Lambert's Law,

Absorbance=Log (1/Transmittance)

If we let the concentration (C) be equal to the hematocrit of the sample, and since b=0.3 cm (the path length of the Spectra cuvette), then it is possible to determine a pseudo-extinction coefficient for the samples (ε') by plotting the absorbance values for the red cell samples versus the product of the hematocrit times the path length. The extinction coefficient for the samples is represented by the slope of this line.

TABLE 3

Determination of Extinction Coefficient for Red Cell Samples.

| T | B | HCT | B*HCT | Absorbance log (1/T) | ε |
|---|---|---|---|---|---|
| 0.995 | 0.3 | 1.3 | 0.39 | 0.002 | .0051 |
| 0.606 | 0.3 | 3.7 | 1.11 | 0.218 | .196 |
| 0.0525 | 0.3 | 6 | 1.8 | 1.280 | .71 |
| 0.097 | 0.3 | 10.2 | 3.06 | 1.013 | .33 |
| 0.104 | 0.3 | 16.3 | 4.89 | 0.983 | .20 |
| 0.036 | 0.3 | 21.8 | 6.54 | 1.444 | .22 |
| 0.0033 | 0.3 | 80.2 | 24.06 | 2.481 | .10 |

Using the values obtained as described above, it was possible to determine a pseudo-extinction coefficient for these samples to be 0.08661.

The value for the extinction coefficient permits calculation of the penetration distance of UV light into red cell samples as a function of the sample hematocrit. For this estimation, the penetration depth of the sample in which 90% of the incident light would be absorbed was determined using the following equation:

A=ε b C

A=1 (90% Absorbance of Incident Light), ε=0.08661, C=Sample hematocrit, b=Path Length.

The values determined using actinometry were compared to those which were calculated previously using estimates taken from UV Spectrophotometric measurements of light absorbance in red cell and platelet samples.

FIG. 2 shows how absorbance and distance from the light source varies for red blood cells, comparing predicted with observed values. These results indicate that, for samples at hematocrits in the region of 80%, it is possible, using the preferred configuration of this invention, to get light into the sample to a depth of 0.14 cm. This represents a flow path width that is less than half the width of the current Spectra cuvette.

Example 6

Effects of Virus Inactivation Treatment on Platelet In Vitro Parameters

Effects of virus inactivation treatment on platelet in vitro parameters were evaluated. Platelet preparations were treated with 7,8-dimethyl-10-ribityl isoalloxazine in combination with UV light. Various in vitro parameters were used as monitors of platelet function in order to determine the extent of changes induced by the treatment conditions. Factors such as energy level of UV light exposure, dose of 7,8-dimethyl-10-ribityl isoalloxazine used, and sample processing conditions were examined for their impact on platelet quality post-treatment. Results from this study are used to establish an appropriate treatment window for inactivation of HIV-1 without compromising platelet function.

Samples were prepared with three different concentrations of 7,8-dimethyl-10-ribityl isoalloxazine. Platelets obtained from a standard Spectra LRS collection were used for these studies.

Starting samples were centrifuged to concentrate the platelet pellet. The pellet was resuspended in a 70:30 (Isolyte S, pH 7.4; McGaw, Inc. Media:Plasma) solution. 7,8-dimethyl-10-ribityl isoalloxazine at the specified concentration, was present in the plasma:media mixture. The platelet suspension was then passed through a UV irradiation chamber at one of three specified flow rates. The flow rates were directly correlated to the energy level of exposure for the cells/media mixture which passes through the irradiation chamber. After flowing through the irradiation chamber, samples were stored in a citrate plasticized sampler bag for subsequent analysis.

Following irradiation, in vitro measurements of platelet function, including hypotonic shock response (HSR), GMP-140 expression, pH, $pCO_2$, $pO_2$, platelet swirl, and cell count, were evaluated in order to determine the effects of the treatment protocol on cell quality.

Platelet quality was monitored as a function of irradiation conditions (sensitizer concentration and flow rates/Energy levels). The platelet quality includes parameters such as HSR response, GMP-140 activation, etc. The flow rates that are studied can be related to the Energy of exposure as follows:

Transit Time (T, sec)=Exposure Time=0.375 mls/($F_r$/60)

$F_r$=Flow Rate (mls/min)

0.375 mls=Cuvette Volume (mls)

$$\therefore T \text{ (sec)} = \frac{22}{F_r}$$

$$\text{Energy (Joules/cm}^2\text{)} = \frac{\text{Flux } (\phi, \text{mW/cm}^2) * T \text{ (sec.)}}{1000}$$

$$E = \frac{\phi * 0.022}{F_r}$$

The effect of energy of UV exposure and concentration of 7,8-dimethyl-10-ribityl isoalloxazine on the stability and viability of treated platelets was evaluated. Three energy levels and three concentration levels were evaluated as follows:

Energy Levels: 1,5,9 $J/cm^{2*}$ 7,8-dimethyl-10-ribityl isoalloxazine

Concentrations: 1, 50, 100 $\mu M$**

Levels of total energy exposure were determined by the flow rate of the suspension through the irradiation chamber in accordance with the conversion chart of Table 4.

Since the media is diluted 70:30 (Media:Plasma) the stock concentration of 7,8-dimethyl-10-ribityl isoalloxazine in media alone prior to mixing with the plasma was adjusted appropriately. This required starting concentrations in Isolyte S of 1.43, 71.4, and 143 $\mu M$.

TABLE 4

Energy Exposure Levels as a Function of Flow Rate Through the Irradiation Chamber

| Energy Delivered (J/cm²) | Flow Rate (mls/min) | Time to process 20 mls (minutes) |
|---|---|---|
| 1 | 16.90 | 1.18 |
| 2 | 8.45 | 2.37 |
| 3 | 5.83 | 3.55 |
| 4 | 4.22 | 4.73 |
| 5 | 3.38 | 5.92 |
| 6 | 2.82 | 7.10 |
| 7 | 2.41 | 8.29 |
| 8 | 2.11 | 9.47 |
| 9 | 1.88 | 10.65 |
| 10 | 1.69 | 11.84 |

Flux = 3640 mW/cm²; chamber volume = 0.117 mls.

Values for treated samples were compared to control groups. The control samples included the following:

Untreated Sample in Plasma (Historical Control)

+Flow-UV-7,8-dimethyl-10-ribityl isoalloxazine

Procedure

A normal donor platelet apheresis product was obtained from an AABB accredited blood banking facility. The sample was collected using standard Spectra LRS procedures. All manipulations or procedures described below were performed with standard laboratory safety procedures and methods. The unit number and blood type were recorded. All samples were used within 24 hours of collection. Aseptic procedure was followed for all sample transfers and processing steps.

The sample was transferred to a 500 mls PVC transfer pack and centrifuged at 5000×g for five minutes to pack the platelets. Plasma was then removed from the platelet pellet using a standard plasma press. The plasma was retained for further use. The plasma removed from the cell pellet was then mixed with a stock solution of Isolyte S, pH 7.4; McGaw, Inc. This stock solution of media was prepared by adding a pre-determined amount of 7,8-dimethyl-10-ribityl isoalloxazine to Isolyte S to provide final concentrations of 1.43, 71.4, and 143 $\mu M$. Following addition of 7,8-dimethyl-10-ribityl isoalloxazine the stock solution was filtered through a 0.22 $\mu M$ sterile filter. The stock solution was then mixed with autologous plasma in a 70:30 (v:v) ratio to provide final 7,8-dimethyl-10-ribityl isoalloxazine concentrations of 1, 50, and 100 $\mu M$ respectively. During preparation of the 7,8-dimethyl-10-ribityl isoalloxazine stock solutions, care was taken to avoid exposure to light. Samples were prepared according as follows:

| | |
|---|---|
| 1 µM | 2 samples |
| 100 µM | 2 samples |
| 50 µM | 1 sample |

The platelet pellet was then resuspended in the plasma-:media mixture to the original volume of the starting sample. The sample was connected to a flow apparatus comprising a container for cells and photosensitizer, a container for media, said containers being connected via valved lines to a single line for mixed cells/sensitizer and media equipped with a pump. Mixed cells/sensitizer and media were flowed into a cuvette held in a holder with a mirrored wall, irradiated by a light source. This irradiation chamber was equipped with a temperature probe. After passing through the cuvette, fluid was collected in a product bag.

The tubing set was initially primed with Isolyte S media. Five minutes prior to the start of the test sample flow, the light source was activated. Temperature was monitored during this interval and kept lower than 32° C. in the irradiation chamber.

The flow rate for the sample through the irradiation chamber was determined by the chart of Table 4. Flow rates which provide total irradiation energy levels of 1, 5 and 9 J/cm² were utilized according to the following testing matrix:

Sample Run #1: 7,8-dimethyl-10-ribityl isoalloxazine Concentration=1 µM
   A. +7,8-dimethyl-10-ribityl isoalloxazine+1 J/cm²
   B. +7,8-dimethyl-10-ribityl isoalloxazine+9 J/cm²
Sample Run #2: 7,8-dimethyl-10-ribityl isoalloxazine=100 µM
   A. +7,8-dimethyl-10-ribityl isoalloxazine+1 J/cm²
   B. +7,8-dimethyl-10-ribityl isoalloxazine+9 J/cm²
Sample Run #3: 7,8-dimethyl-10-ribityl isoalloxazine=50 µM
   A. +7,8-dimethyl-10-ribityl isoalloxazine+5 J/cm²
Sample Run #4: Control Sample, 7,8-dimethyl-10-ribityl isoalloxazine=0 µM
   A. +Flow-UV-7,8-dimethyl-10-ribityl isoalloxazine All samples were identified by the run number and sample letter designation corresponding to treatment condition (i.e., 1A). Each sample set was run for a total of 2 replicates. The order in which samples were treated was determined by assignment according to a random number generator.

A sample volume of 20 mls per run condition was collected for each sample. These samples were collected into citrate plasticized sampling bags (53 mls total volume) and stored for analysis. The temperature of the sample and the irradiation chamber was noted at the start, mid-point, and end of each run.

An initial aliquot from each preparation was removed post-treatment for analysis. Parameters for analysis included cell count, pH, $pCO_2$, $PO_2$, platelet swirl, HSR, and GMP-140 analysis. The remaining portion of the sample was placed in an end-over-end platelet agitator in a +22 incubator and stored for five days post-treatment. On day 5, a second aliquot was removed and analyzed for the same in vitro parameters.

The following equipment was used: Nikon Labophot microscope; Serono-Baker System 9000 Hematology Analyzer; analytical balance; platelet incubator (+22 Celsius) and rotator; laboratory refrigerator (+4 Celsius); Mistral 3000i Centrifuge; Corning Blood Gas Analyzer; Becton-Dickinson FACSCALIBUR Flow Cytometer; UV irradiation chamber; UV radiometer (UVX Radiometer, UVP, Inc.); EFOS Ultracure 100SS Plus (365 nm maximum output and 340 nm bandpass filters); and temperature probe (thermocouple).

Results for each set of test variables were compared for the defined conditions of energy of exposure and concentration of 7,8-dimethyl-10-ribityl isoalloxazine. Direct comparison to the untreated control sample was made and significant differences defined by a probability $p>0.05$ from a paired, one-tailed, Student's T-Test analysis.

The results from these studies were summarized as follows:

1. At sensitizer concentrations in excess of 10 µM and platelet concentrations above 1.5E+06/µL, there was a drop in sample pH by day 2. The pH declined steadily beyond day 2 of storage reaching unacceptable levels (<6.5) by day 3 of storage. All other in vitro parameters followed the pattern observed with sample pH.
2. This decrease in sample pH occurred regardless of whether or not the sample was exposed to UV light.
3. At platelet concentrations of 5.4E+05/µL, there was no drop in sample pH after extended storage at any sensitizer concentration studied up to 100 µM.
4. At sensitizer concentrations up to 10 µM, platelet concentrations above 1.5E+06/µL, and UVA levels up to 10 J/cm², measured platelet properties were comparable to control, untreated cells. These remained comparable to control levels after five or more days of storage post-treatment.

These studies on platelet function post-treatment provided a clear window in which cell properties were maintained at levels comparable to untreated cells. The results also indicated that by varying the storage or treatment conditions for the cells this window can be expanded. The observed effect of 7,8-dimethyl-10-ribityl isoalloxazine with or without UV light on sample pH suggests a metabolic effect of this additive which may be moderated by changes in the storage or processing conditions of the samples.

Example 7

Measurements of Shear Stresses on Red Cells As a Function of Flow Rate and Sample Hematocrit The low levels of UV light penetration into red cell samples at high hematocrits raised the need to understand the effects of passing red cells through narrow openings in the light path. Reduction in sample thickness in the light path should increase delivery of UV dose at high sample hematocrits. In order to confirm this approach, several pressure drop measurements were undertaken using openings of varying dimensions. A pressure gauge was placed in line with a peristaltic pump both upstream and downstream from the narrowed openings. Whole blood of varying hematocrits was passed through the openings at controlled flow rates. Differences in the pressure readings at both locations permitted direct measurement of the pressure drop across the opening. Using this value and the dimensions of the opening, it was possible to determine the shear stress experienced by the red cells as they passed through the narrowed cell using the following equation:

$$\Delta P = \frac{8\mu l Q}{g d^3 w} \quad \text{Pressure Drop}$$

$$\tau_w = \frac{4\mu Q}{g w d^2} \quad \text{Shear Stress}$$

For blood,
   $\mu$=Viscosity=0.0125/(1-Hematocrit)
   g=gravitational constant=981
   Q=Flow Rate=mls/sec
   l, w, d=Dimensions of opening in cm

TABLE 5

Measurement of Shear Stress on Red Cells
As Functions of Flow Rate and Sample Hematocrit

| | | 0.08 × 0.008 | Dpmeas (dynes/cm$^2$) | 0.08 × 0.008 | Dpmeas (dynes/cm$^2$) | 0.08 × 0.008 | Dpmeas (dynes/cm$^2$) |
|---|---|---|---|---|---|---|---|
| 41% HCT | Q = 3.38 | 1.5 | 95.9 | 1.0 | 77.6 | 0.0 | 0.0 |
| 64% HCT | Q = 3.38 | 4.0 | 255.8 | 3.0 | 232.9 | 2.0 | 182.1 |
| 41% HCT | Q = 16.9 | 9.7 | 618.4 | 7.0 | 543.4 | 4.7 | 425.3 |
| 61% HCT | Q = 16.9 | 20.7 | 1321.9 | 12.3 | 957.2 | 8.7 | 789.6 |
| 41% HCT | Q = 3.38 | 2.0 | 93.7 | 1.0 | 60.3 | 1.0 | 73.5 |
| 64% HCT | Q = 3.38 | 4.5 | 210.8 | 3.0 | 180.9 | 2.0 | 146.9 |
| 41% HCT | Q = 16.9 | 12.7 | 593.6 | 7.0 | 422.1 | 4.7 | 343.0 |
| 61% HCT | Q = 16.9 | 23.3 | 1093.0 | 14.7 | 884.6 | 12.0 | 881.4 |
| 41% HCT | Q = 3.38 | 3.0 | 97.4 | 1.2 | 49.2 | 1.0 | 49.0 |
| 64% HCT | Q = 3.38 | 6.5 | 211.0 | 3.5 | 143.5 | 2.0 | 97.9 |
| 41% HCT | Q = 16.9 | 15.3 | 497.7 | 8.3 | 341.6 | 5.7 | 277.6 |
| 61% HCT | Q = 16.9 | 35.7 | 1158.1 | 18.0 | 738.1 | 12.7 | 620.4 |

In previous experiments, it was determined that shear stresses of 1,000–2,000 dynes/cm$^2$ for intervals of 1–10 minutes or levels of 5,000–7,000 dynes/cm$^2$ for intervals of approximately 10 msec were sufficient to induce red cell hemolysis. Only in the case of the highest sample hematocrit (61%) and highest flow rate (16.9) did values exceed 1,000 dynes/cm$^2$. This occurred only for openings of the narrowest width (0.008 inches).

Values for the light penetration depth using the proposed configuration indicate that delivery in sufficient UV energy to drive virus inactivation processes is achievable even for samples with high hematocrits.

Results from shear stress analysis on red cell samples subjected to flow indicate that flow path dimensions may be significantly reduced and high flow rates maintained without risking red cell hemolysis.

Example 8

A platelet concentrate was mixed with the platelet additive solution Isolyte S at a ratio of 20:80 platelet concentrate:Isolyte S. Mixtures of platelet concentrates and platelet additive solutions are referred to herein as in "media." Platelet concentrate without additive solution is referred to herein as in "plasma." Both were spiked with *Listeria monocytogenes*. Vitamin K5 was then added to each in the amount of 300 μg/mL B. Each was then exposed to UV, visible or room light in the cuvette apparatus of FIG. 7 with the results shown in Table 6.

TABLE 6

| | Log Inactivation (cfu/mL) | |
|---|---|---|
| | K5 in Media | K5 in Plasma |
| UV, 40 J/$cm^2$ | 4.2 Logs | 0.1 Logs |
| VIS, 40 J/$cm^2$ | 4.2 Logs | 0.1 Logs |
| Room Light | 0 Logs | 0 Logs |

UV Light = 365 nm
VIS Light = 419 nm
Pathogen = *Listeria monocytogenes*
Concentration of K5 = 300 μg/mL Example 9

Media and plasma as described above containing vitamin K5 were spiked with bacteria and irradiated or exposed to room light only (K5-light) as shown in Table 7, and growth evaluated after three days of incubation. Inactivation of some species was seen in the absence of irradiation.

TABLE 7

| | | Media | | Plasma | |
|---|---|---|---|---|---|
| | Spike Level (cfu/mL) | K5 + Light | K5 − Light | K5 + Light | K5 − Light |
| P. aeruginosa | 3.4 Logs | − | − | − | − |
| S. aureus | 2.1 Logs | − | − | + | + |
| S. epidermidis | 3.2 Logs | − | + | − | − |
| L. monocytogenes | 3.5 Logs | − | − | + | + |
| E. coli | 3.1 Logs | − | − | + | − |

UV Light = 365 nm, 40 J/$cm^2$
+= Growth detected after three days incubation
−= No Growth detected after three days incubation
Concentration of K5 = 300 μ/mL Example 10

Media made using a platelet concentrate as described in Example 8 and Isolyte S at a ratio of Isolyte S:platelet concentrate of 70:30 and containing 300 μg/mL vitamin K5 was spiked with several species of bacteria and irradiated at energy levels of 30 and 60 J/$cm^2$. Inactivation as a function of energy of irradiation is set forth in Table 8 and FIG. 8.

TABLE 8

| Energy (J/$cm^2$) | S. aureus | S. epidermidis | L. monocytogenes | E. coli |
|---|---|---|---|---|
| 0 | 4.3 | 2.6 | 2.8 | 3.5 |
| 30 | 3.6 | 2.7 | 2 | 2 |
| 60 | 3.2 | 2.5 | 1 | 1 |

Example 11

To platelet concentrate as described in Example 8 and to 70:30 media as described in Example 10 was added 10 μM of 7,8-dimethyl-10-ribityl isoalloxazine. The platelet concentrate and media were spiked with *S. aureus* or *S. epiderrnidis*, and irradiated at 80 J/$cm^2$ and 30 J/$cm^2$ and inactivation measured as above. Results are shown in FIG. 9.

Example 12

To plasma concentrate as described in Example 8 contained in a standard blood bag was added 25 μM 7,8-dimethyl-10-ribityl isoalloxazine in powder form. The bag was spiked with bacteria as shown in Table 9, agitated and exposed to 120 J/cm² radiation. Inactivation results are set forth in Table 9.

TABLE 9

| Pathogen | Log Inactivation (cfu/mL) |
| --- | --- |
| S. aureus | 1.7 Logs |
| S. epidermidis | 3.5 Logs |
| P. aeruginosa | 3.6 Logs |
| E. coli | 4.1 Logs |

Example 13

To platelet concentrate as described in Example 8 was added 7,8-dimethyl-10-ribityl isoalloxazine, alloxazine mononucleotide, or 7-8-dimethyl alloxazine, followed by spiking with S. aureus or S. epidermidis, and irradiation at 80 J/cm². Inactivation results are shown in Table 10.

TABLE 10

| | Log Inactivation (cfu/mL) | |
| --- | --- | --- |
| | Staphylococcus aureus | Staphylococcus epidermidis |
| 7,8-dimethyl-40-ribityl isoalloxazine, 10 μM | 1.9 Logs | 4.1 Logs |
| alloxazine mononucleotide, 10 μM | 1.6 Logs | 5.6 Logs |
| 7-8-dimethyl alloxazine, 7 μM | 1.6 Logs | 2.9 Logs |

Example 14

Figure 10:
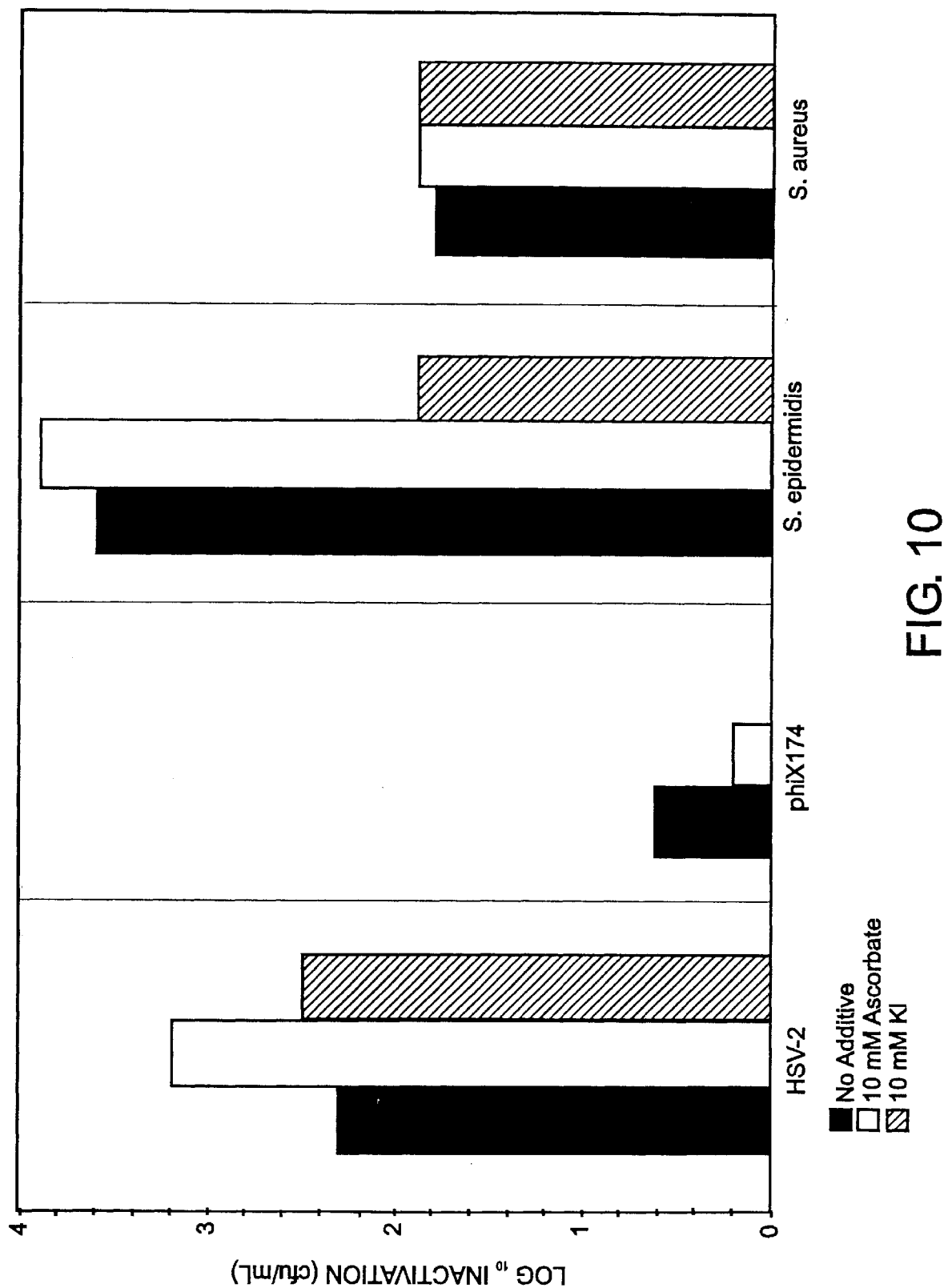
FIG. 10 shows the effect on inactivation of virus, bacteriophage and bacteria of adding antioxidants to platelet concentrate.

To platelet concentrate of Example 8 was added 10 μM 7,8-dimethyl-10-ribityl-isoalloxazine. Aliquots contained no additive, 10 mM ascorbate or 10 mM KI as a "quencher" or antioxidant. The solutions were spiked with HSV-2, ΦX 174, S. epidermidis or S. aureus and irradiated at 80 J/cm². Results are shown in FIG. 10.

Example 15

Figure 11:
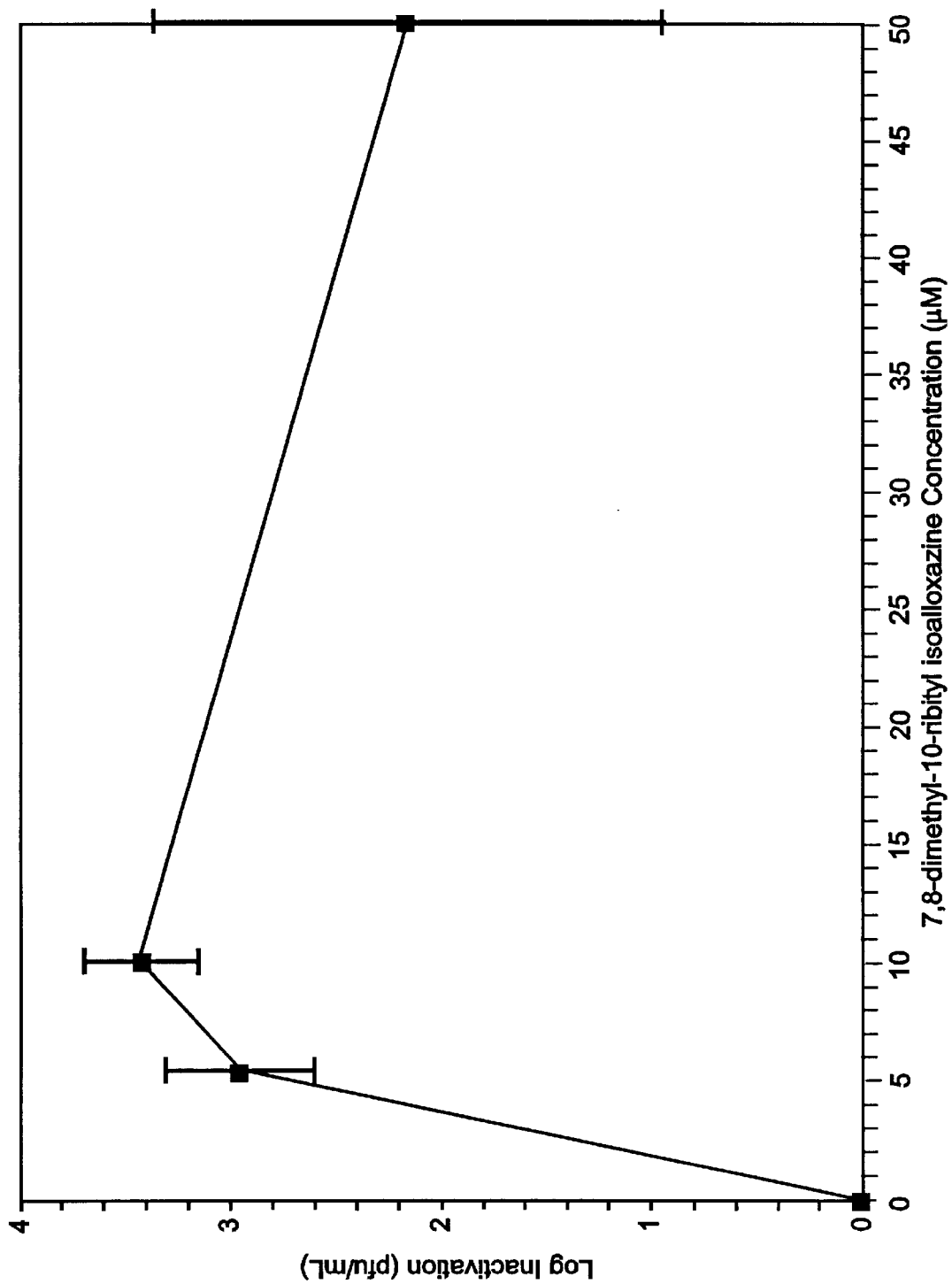
FIG. 11 shows the inactivation curve for Herpes Simplex type II virus as a function of concentration of photosensitizer at an energy of irradiation of 20J/cm$^2$ using half ultraviolet and half visible light.

To platelet concentrates of Example 8 were added varying concentrations of 7,8-dimethyl-10-ribityl-isoalloxazine. These solutions were spiked with herpes simplex virus type II (HSV-II), a double-stranded DNA envelope virus. Irradiation was done at 80 J/cm². The experiment was replicated three times. In all three trials complete inactivation was achieved. Results are shown in FIG. 11.

Example 16

Figure 12:
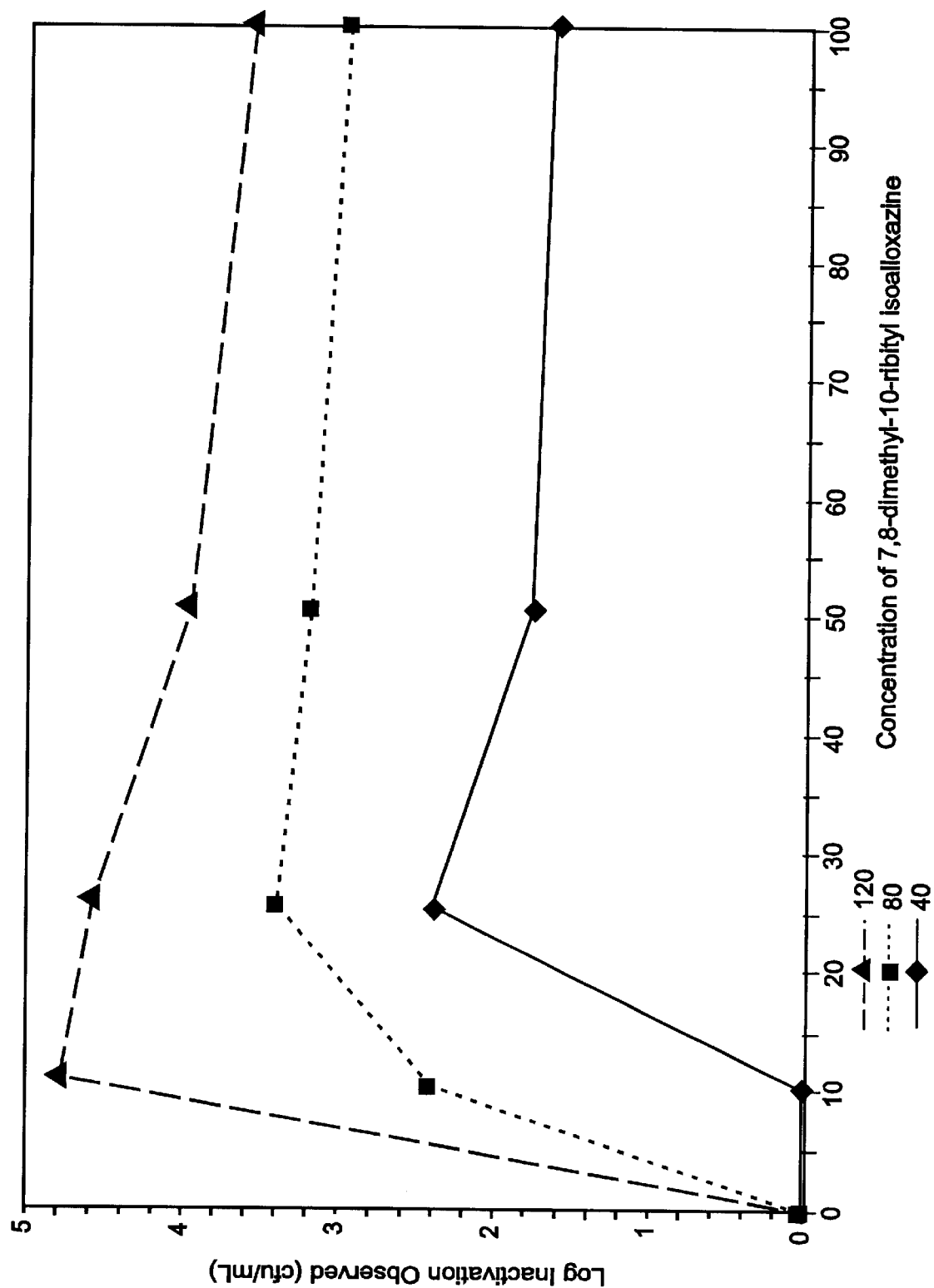
FIG. 12 shows inactivation of S. epidermidis at varying concentrations of photosensitizer and energies of irradiation.

The protocol of Example 15 was followed using S. epidermidis instead of HSV II at energies of irradiation of 40, 80 and 120 J/cm². Inactivation results are shown in FIG. 12.

Example 17

Figure 13:
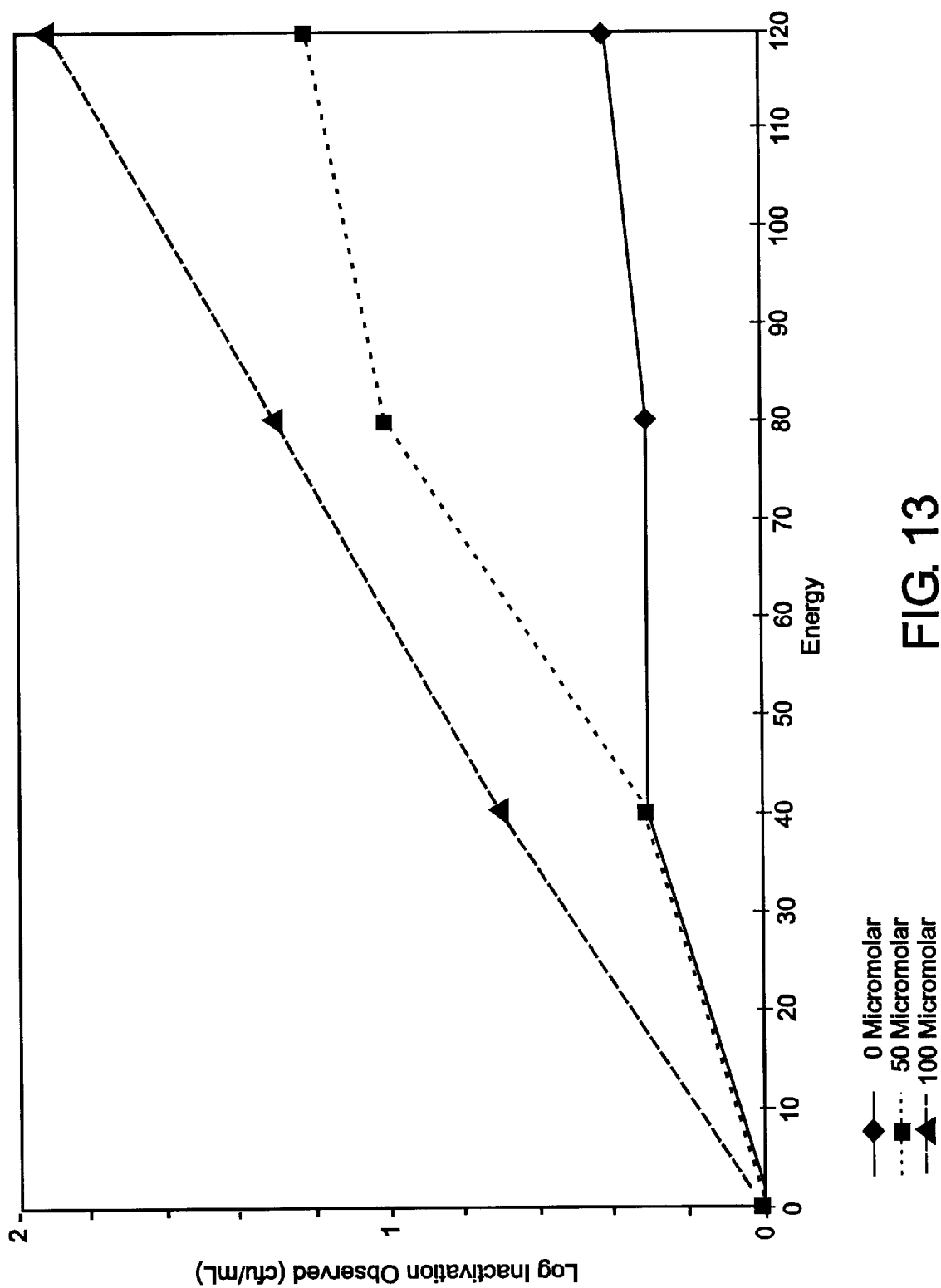
FIG. 13 shows inactivation of ΦX174 at varying concentrations of photosensitizer and energies of irradiation.

The protocol of Example 15 was followed using ΦX174, a single stranded DNA bacteriophage, at varying concentrations of 7,8-dimethyl-10-ribityl-isoalloxazine and energies of irradiation. Inactivation results are shown in FIG. 13.

Example 18

Figure 14:
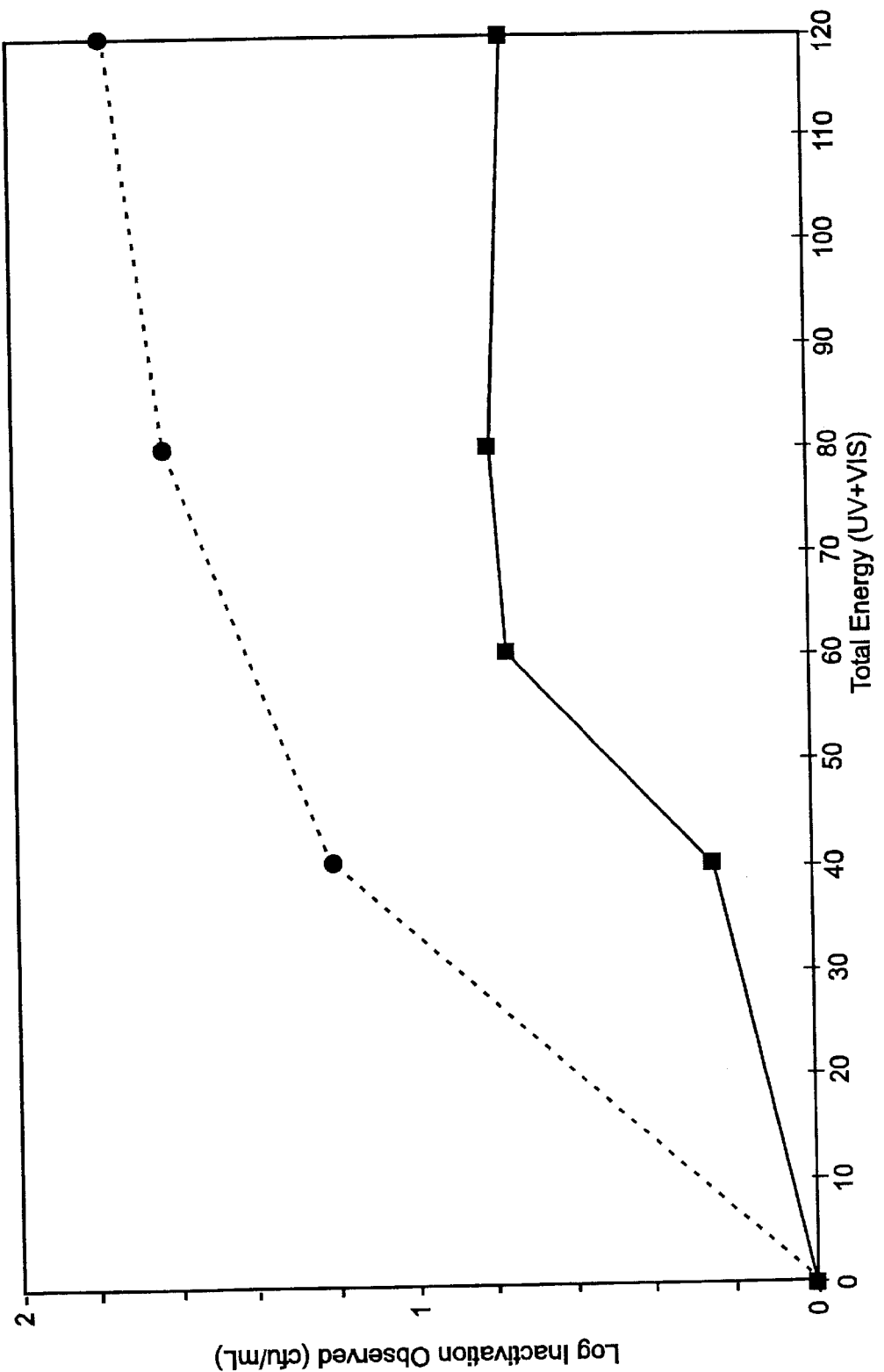
FIG. 14 shows inactivation of S. aureus and ΦX174 at varying energies of irradiation using a 50:50 mixture of ultraviolet and visible light.

To platelet concentrates of Example 8 was added 10 μM 7,8-dimethyl-10-ribityl-isoalloxazine. These were spiked with S. aureus or ΦX174 and irradiated at varying energies of irradiation with a 50:50 mixture of visible and ultraviolet light. Inactivation results are shown in FIG. 14.

Example 19

Figure 15:
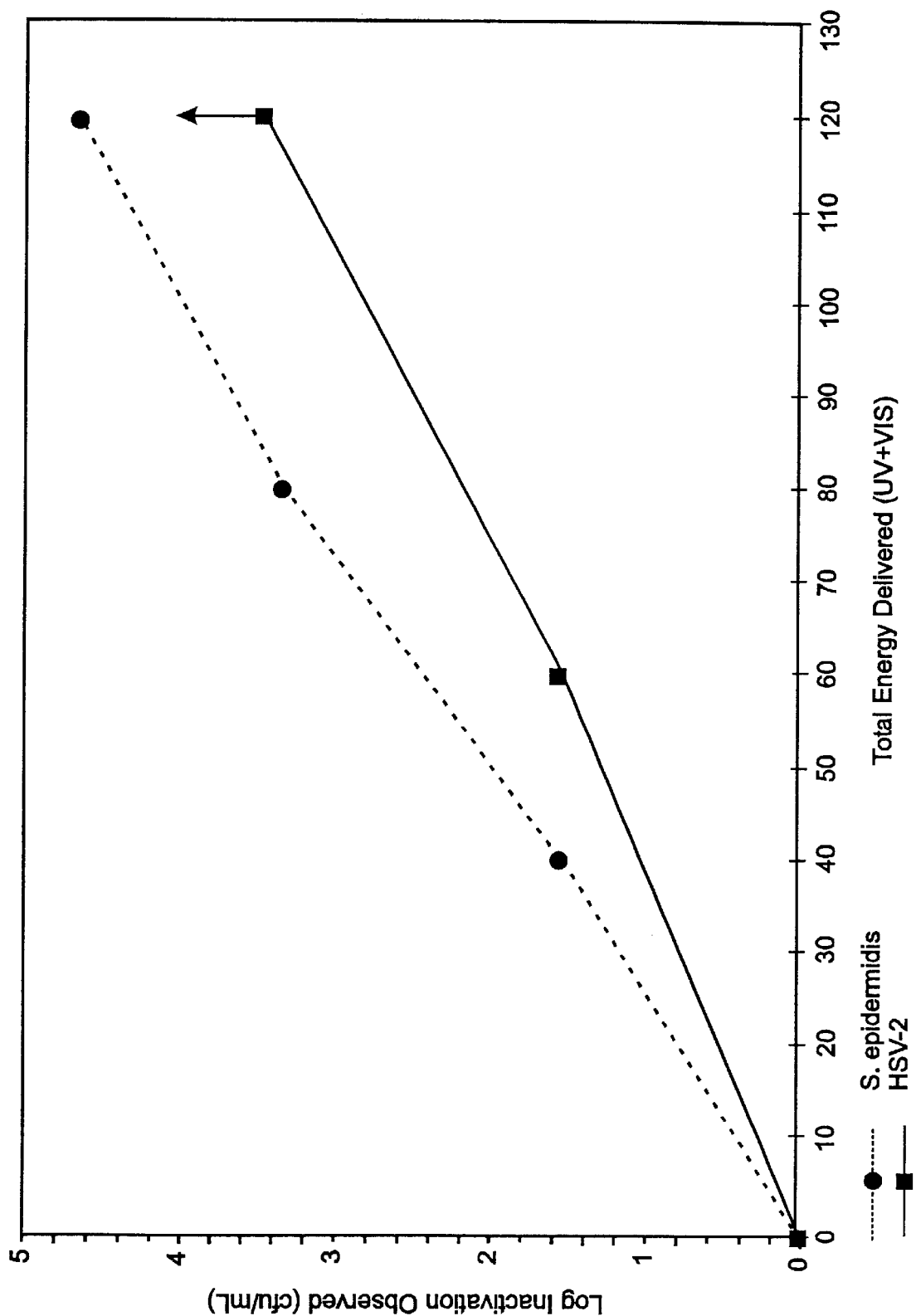
FIG. 15 shows inactivation of S. epidermidis and HSV-II at varying energies of irradiation using a 50:50 mixture of ultraviolet and visible light.

The protocol of Example 18 was followed using S. epidermidis and HSV-II as the microorganisms. A 50:50 mixture of ultraviolet and visible light was supplied by DYMAX light source. Inactivation results are shown in FIG. 15.

Example 20

Figure 16:
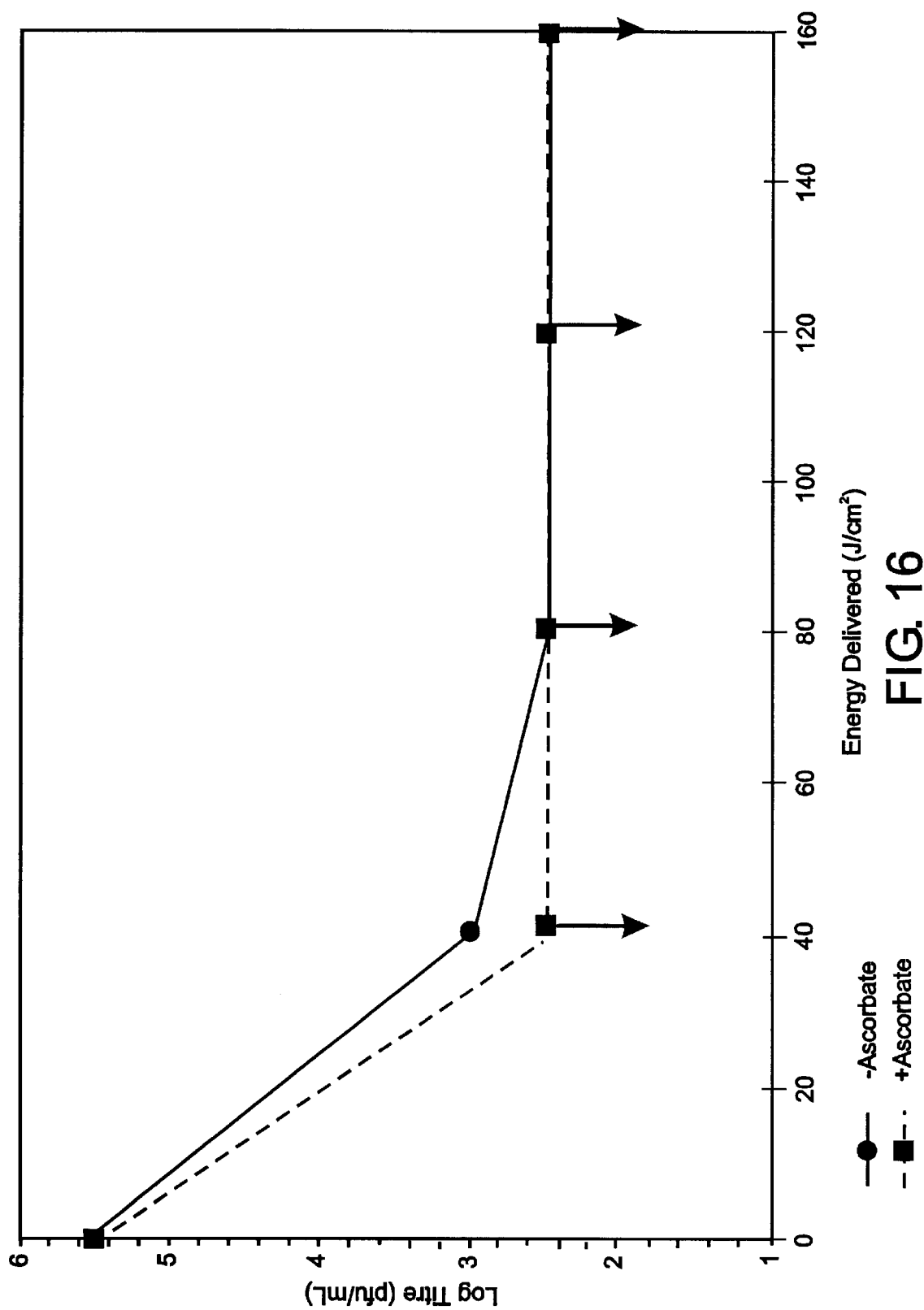
FIG. 16 shows inactivation of HSV2 virus in blood bags agitated and irradiated at varying energy levels.

To platelet concentrate of Example 8 was added 10 μM 7,8-dimethyl-10-ribityl-isoalloxazine in powdered form. Tests with and without added ascorbate were conducted. 150 ml of the test solutions were placed in a Spectra™ blood bag and shaken and exposed to varying energies of irradiation using 50:50 visible:ultraviolet light. After receiving 40 J/cm², the contents of each bag were transferred to a new bag to avoid errors due to microorganisms which may have remained in the spike port of the bag. Inactivation results are shown in FIG. 16. Downward arrows indicate inactivation to the level it was possible to detect (2.5 log titre).

Example 21

Figure 17:
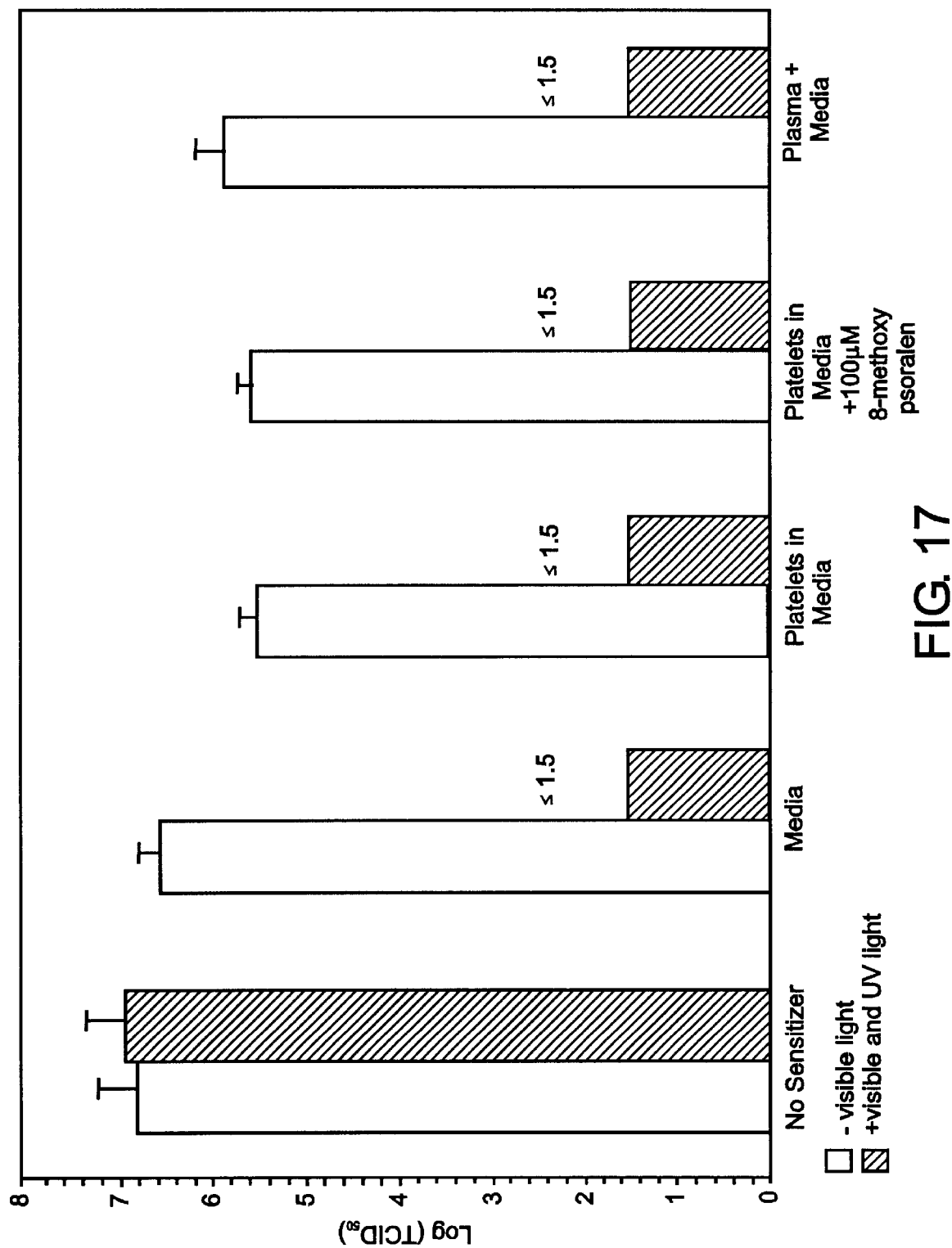
FIG. 17 compares inactivation results for vaccinia virus in various fluids using ultraviolet light alone or 50:50 visible and ultraviolet light.

To platelet concentrate of Example 8 and platelet concentrate in Isolyte S at 30:70 platelet concentrate:Isolyte S, was added 20 μM 7,8-dimethyl-10-ribityl-isoalloxazine. These were spiked with vaccinia virus, a double stranded DNA envelope virus, and exposed to 60 J/cm² visible light or mixed (50:50) visible and ultraviolet light using a DYMAX 2000 UV light source for 30 minutes. The limit of detection was 1.5 logs. Inactivation results are show in FIG. 17. Comparisons were done using no photosensitizer, photosensitizer in Isolyte S media alone, platelets in Isolyte S media, platelets in Isolyte S media using 8-methoxy psoralen instead of 7,8-dimethyl-10-ribityl-isoalloxazine, and platelet concentrate in Isolyte media (30:70).

Example 22

Figure 18:
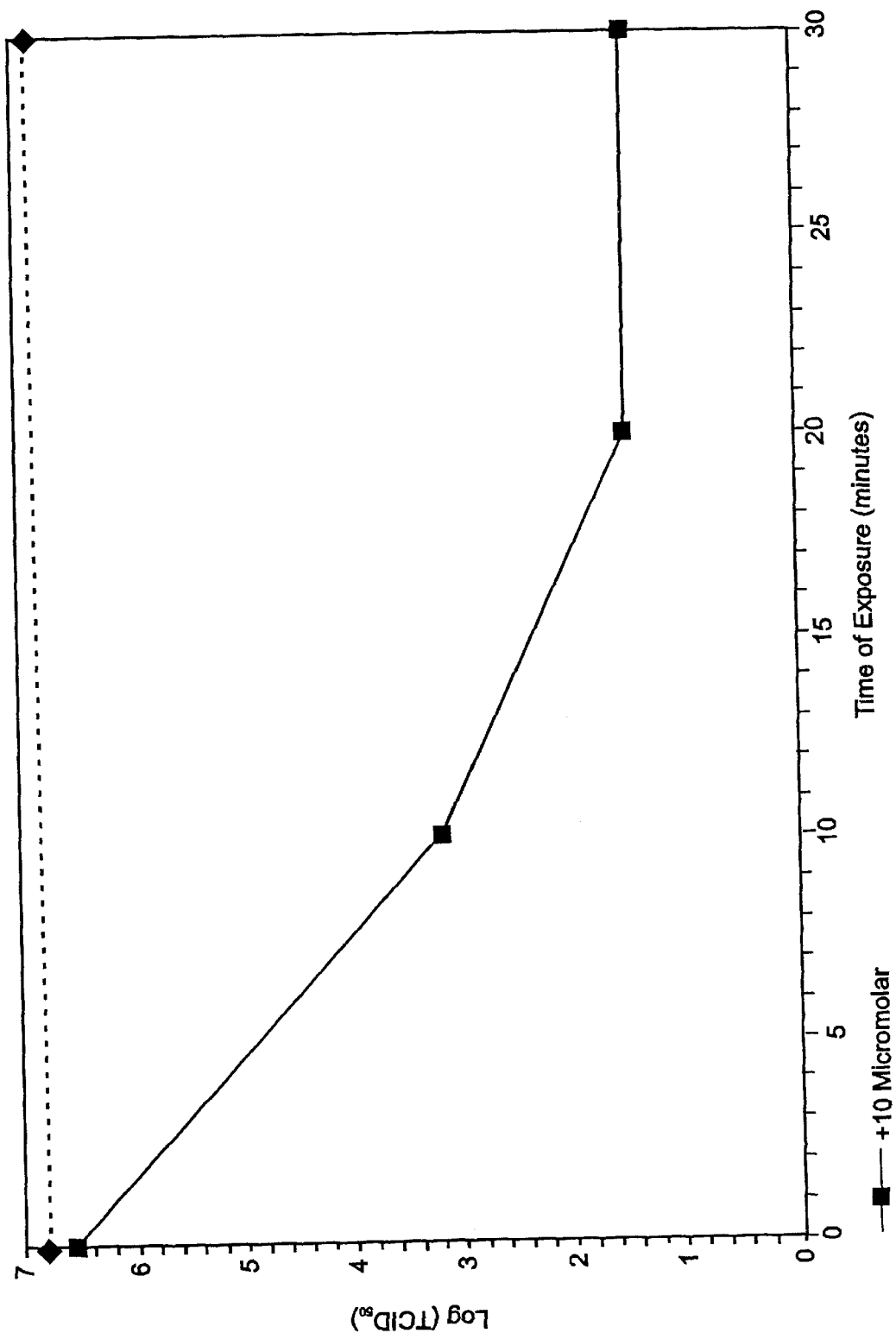
FIG. 18 compares inactivation results with and without sensitizer of vaccinia virus at varying irradiation times.

Samples of platelet concentrate in Isolyte S media 30:70, with and without 10 μM 7,8-dimethyl-10-ribityl-isoalloxazine were spiked with vaccinia virus and irradiated at 60 J/cm² with 50:50 visible:UV light for varying periods of time and inactivation results compared as shown in FIG. 18.

Example 23

Figure 19:
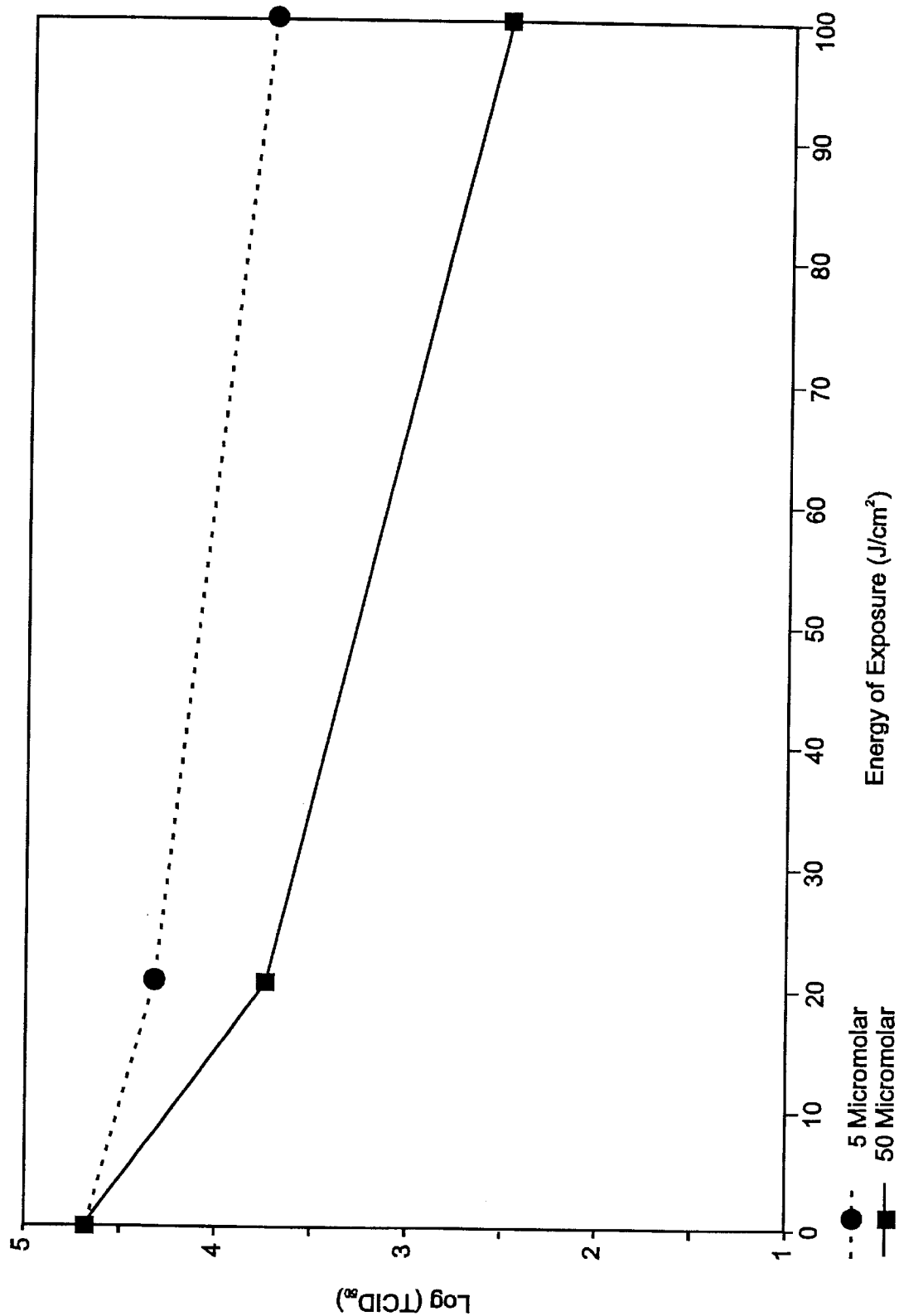
FIG. 19 compares inactivation of extracellular HIV-1 at 5 and 50 $\mu$M of photosensitizer and varying irradiation energies.

To samples of platelet concentrate as described in Example 8 were added 5μM or 50 μM 7,8-dimethyl-10-ribityl-isoalloxazine. Samples were spiked with HIV 1. Using the cuvette flow cell shown in FIG. 7, samples were irradiated with 50:50 visible:UV light at varying energies using an EFOS light system. Inactivation results are show in FIG. 19.

Example 24

Figure 20:
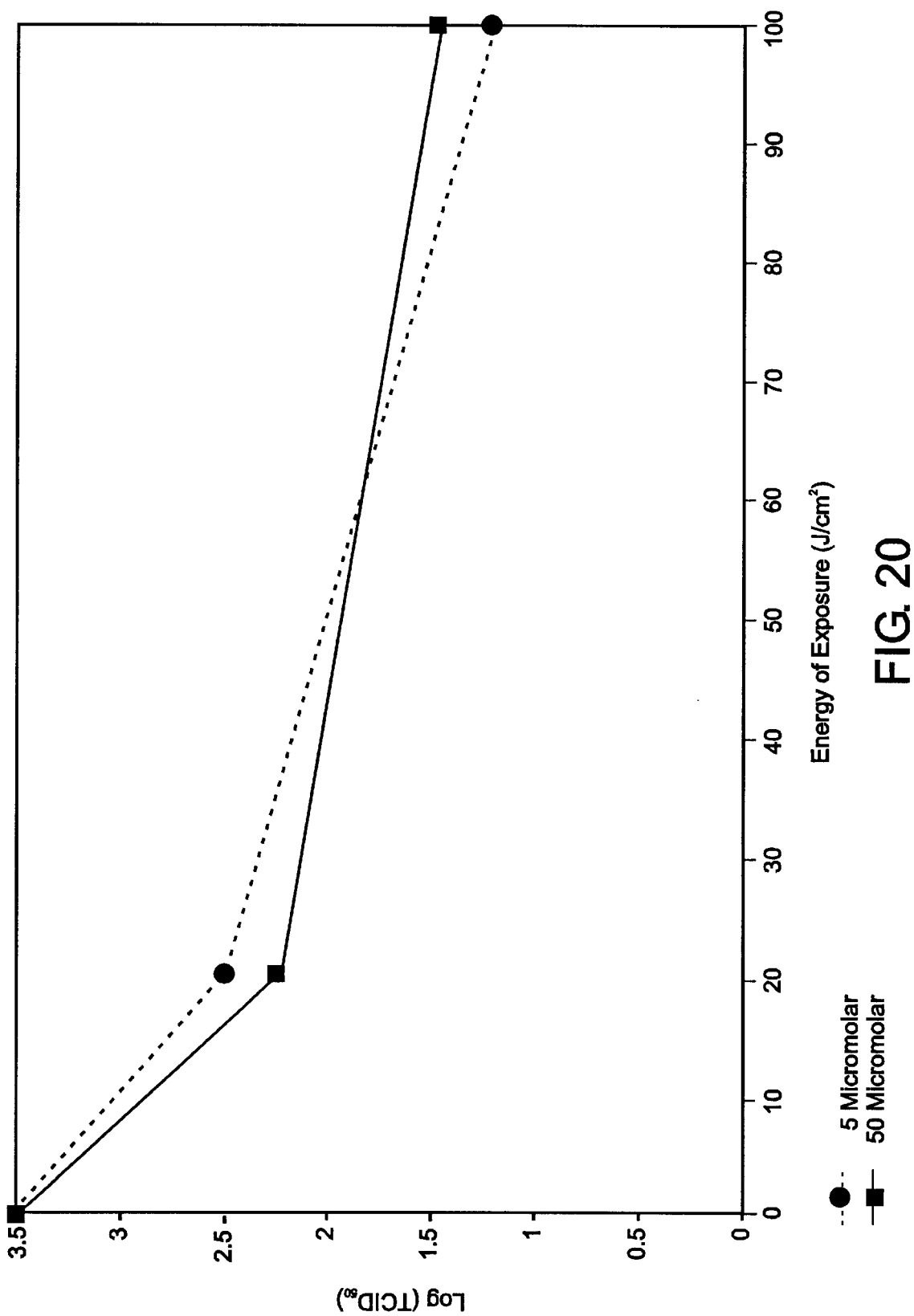
FIG. 20 compares inactivation of intracellular HIV-1 at 5 and 50 $\mu$M of photosensitizer and varying irradiation energies.

HIV-infected ACH-2 cells were added to samples of platelet concentrate described in Example 8. 5 or 50 μM of 7,8-dimethyl-10-ribityl-isoalloxazine were added to the samples. The protocol of Example 23 was followed, and inactivation results are shown in FIG. 20. The presence of HIV was assayed by its cytopathic effect on test cells.

Example 25

Figure 21:
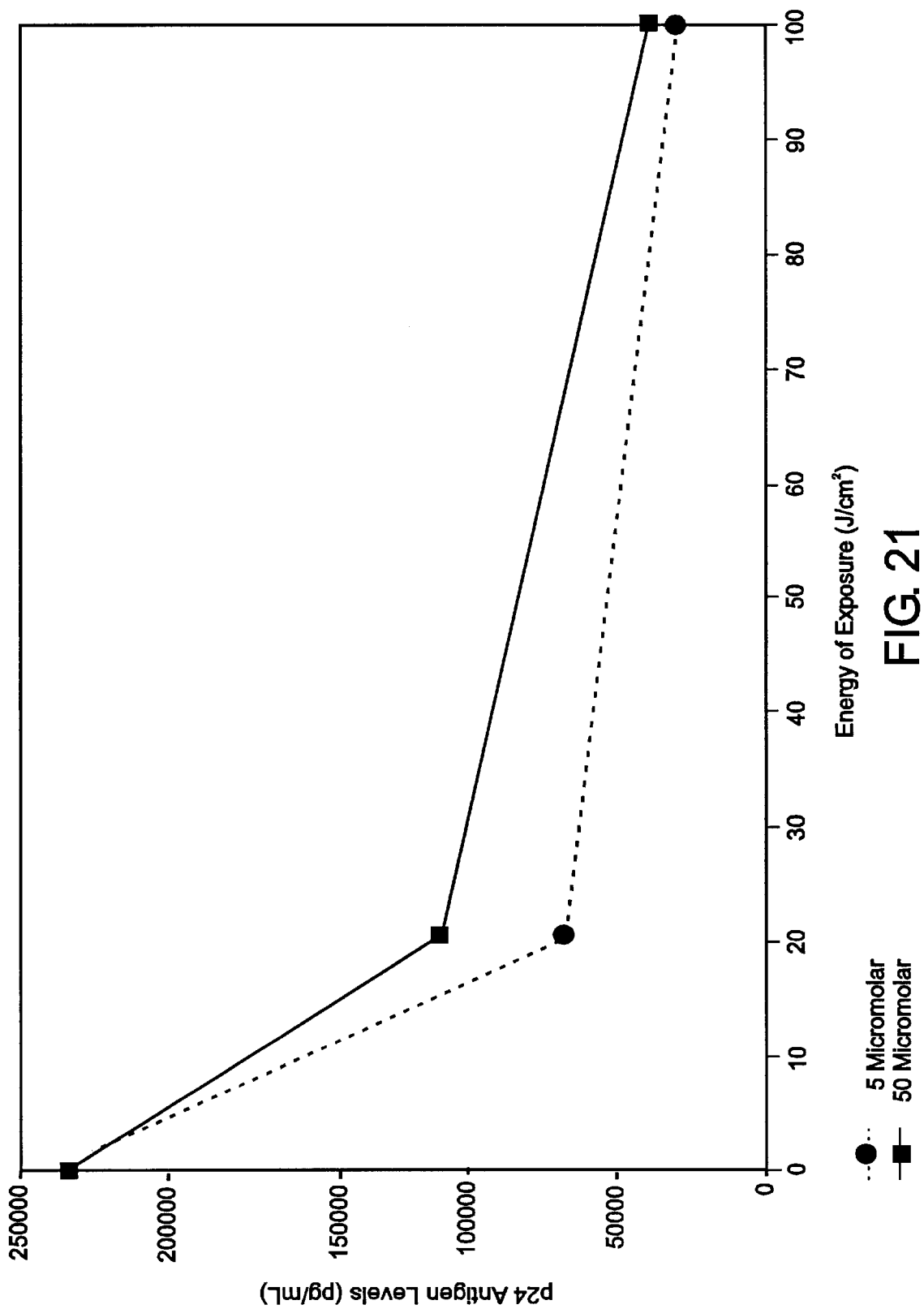
FIG. 21 compares inactivation of intracellular HIV-1 at 5 and 50 $\mu$M of photosensitizer and varying irradiation energies, using p24 antigen levels.

The protocol of Example 24 was followed and the presence of HIV assayed by quantifying the level of P24 antigen production. Inactivation results are show in FIG. 21.

Example 26

Figure 22:
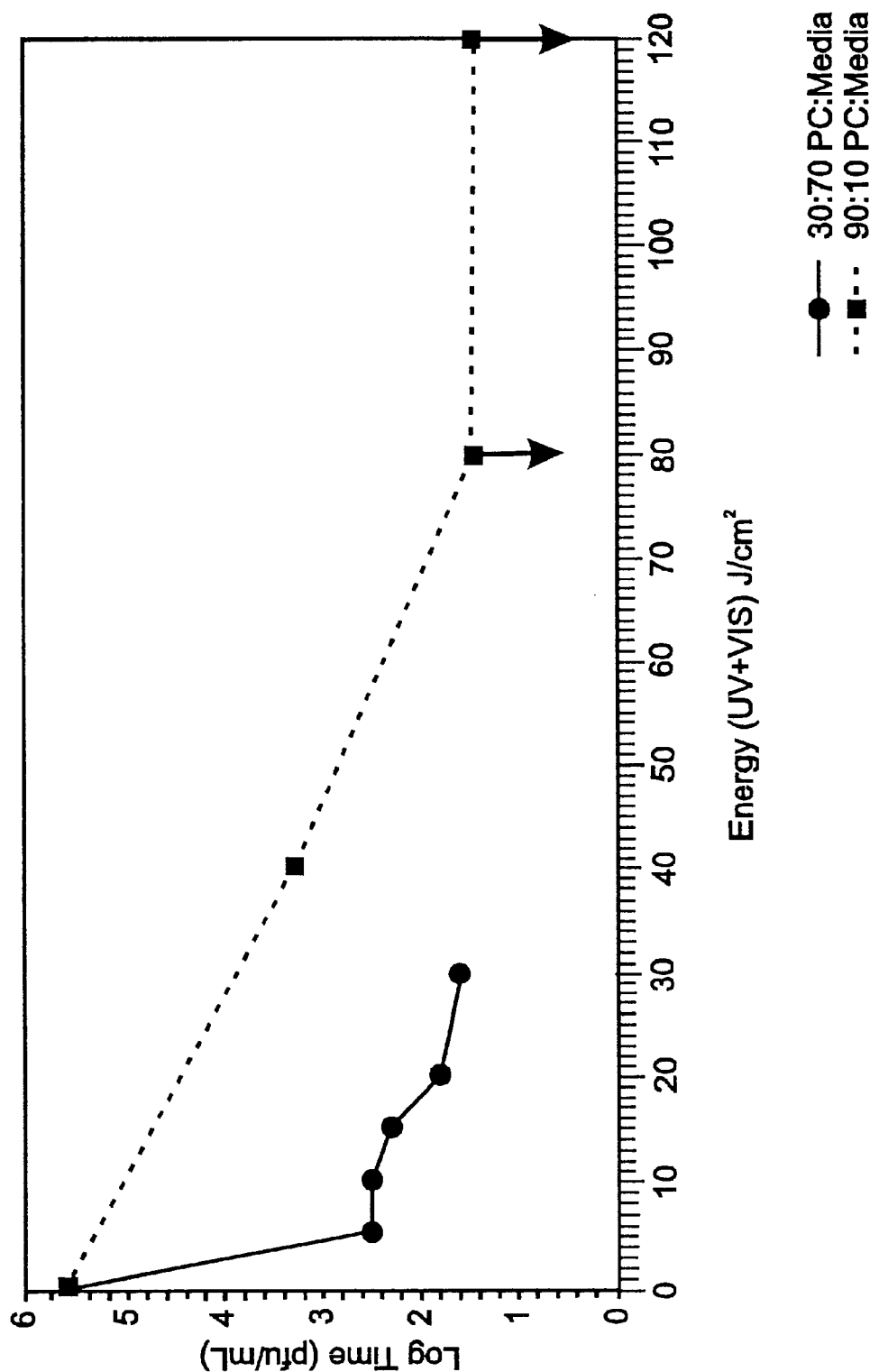
FIG. 22 shows inactivation of HSV-II at varying irradiation levels using platelet concentrate and platelet concentrate in media containing platelet additive solution with ascorbate.

To samples of platelet concentrate as described in Example 8 and media containing 30% platelet concentrate and 70% PASIII™ media were added 6 mM ascorbate and 14 μM 7,8-dimethyl-10-ribityl-isoalloxazine. Samples were spiked with HSV-II. Inactivation results are show in FIG. 22 and Table 11.

TABLE 11

| Time (Minutes) | Energy (UV + VIS) J/cm² | 30:70 PC:Media log virus titre | Energy (UV + VIS) J/cm² | 90:10 PC:Media log virus titre |
|---|---|---|---|---|
| 0 | 0 | 5.6 | 0 | 5.6 |
| 1.5 | 5 | 2.5 | 40 | 3.3 |
| 3 | 10 | 2.5 | 80 | 1.5 No Detectable Virus |
| 4.5 | 15 | 2.3 | 120 | 1.5 No Detectable Virus |
| 6 | 20 | 1.8 | | |
| 9 | 30 | 1.6 | | |
| 12 | 40 | | | |
| 24 | 80 | | | |
| 36 | 120 | | | |

It will be readily understood by those skilled in the art that the foregoing description has been for purposes of illustration only and that a number of changes may be made without departing from the scope of the invention. For example, other photosensitizers than those mentioned may be used, preferably photosensitizers which bind to nucleic acid and thereby keep it from replicating, and more preferably those which are not toxic and do not have toxic breakdown products. In addition, equivalent structures to those described herein for constructing a flow-through system for decontamination of fluids using photosensitizers may be readily devised without undue experimentation by those skilled in the art following the teachings hereof.

What is claimed is:

1. A system for treating a fluid to inactivate microorganisms which may be present therein comprising:
   (a) an endogenous or endogenously-based derivative photosensitizer other than a porphyrin;
   (b) a container adapted to contain said fluid and said endogenous or endogenously-based derivative photosensitizer, said container being equipped with input means, and having a photopermeable surface sufficient to allow exposure of the fluid therein to an amount of photoradiation sufficient to activate the photosensitizer;
   (c) at least one photoradiation source for providing sufficient photoradiation to the fluid in said container of an appropriate wavelength and amount selected to activate the photosensitizer.

2. The system of claim 1 wherein said photoradiation source provides light in the visible spectrum.

3. The system of claim 1 wherein said photoradiation source provides light in the ultraviolet spectrum.

4. The system of claim 1 wherein said at least one photoradiation source provides light in both the visible and ultraviolet spectrum.

5. The system of claim 1 also comprising a photoradiation enhancer.

6. The system of claim 5 wherein said photoradiation enhancer comprises a reflective surface.

7. The system of claim 1 comprising a light guide for conducting photoradiation from said photoradiation source to said photopermeable container.

8. The system of claim 1 also comprising a temperature monitor.

9. The system of claim 1 also comprising means for flowing said fluid into and out of said container.

10. The system of claim 1 also comprising means for agitating said fluid in said container.

11. An apparatus for separating whole blood into blood components comprising the system of claim 1.

12. A system for inactivation of microorganisms in a fluid containing such microorganisms comprising:
   (a) an endogenous or endogenously-based derivative photosensitizer other than an endogenous porphyrin;
   (b) means for adding an effective amount of said photosensitizer to said fluid;
   (c) a photopermeable container for said fluid in fluid communication with said means for adding photosensitizer having a depth and length selected to allow exposure of the fluid of step (b) therein to an amount of photoradiation sufficient to activate the photosensitizer at a selected flow rate;
   (d) means for producing said selected flow rate of said fluid through said container; and
   (e) at least one photoradiation source for providing sufficient photoradiation to the fluid in said container of an appropriate wavelength and amount selected to activate the photosensitizer.

* * * * *

UNITED STATES PATENT AND TRADEMARK OFFICE
CERTIFICATE OF CORRECTION

PATENT NO. : 6,277,337 B1
DATED : August 21, 2001
INVENTOR(S) : Goodrich Jr. et al.

It is certified that error appears in the above-identified patent and that said Letters Patent is hereby corrected as shown below:

Column 10,
Line 15, please replace "method of claim 1." with -- above methods. --.
Line 53, please replace "KS" with -- K5 --.

Column 13,
Line 4, please replace "5,290,221, 5,536,238, 5,290,221 and 5,536,238." with -- 5,290,221 and 5,536,238. --.

Column 22,
Table 3, column 3, row 5, replace "1O.2" with -- 10.2 --.

Column 24,
Line 7, before "Levels" please insert -- * --.
Line 10, before "Since" please insert -- ** --.

Column 27,
Table 5, please replace Table 5 with the following:

UNITED STATES PATENT AND TRADEMARK OFFICE
CERTIFICATE OF CORRECTION

PATENT NO. : 6,277,337 B1
DATED : August 21, 2001
INVENTOR(S) : Goodrich Jr. et al.

It is certified that error appears in the above-identified patent and that said Letters Patent is hereby corrected as shown below:

Table 5: Measurement of Shear Stress on Red Cells As Functions of Flow Rate and Sample Hematocrit

|  |  | 0.08 X 0.008 | Dpmeas (dynes/cm$^2$) | 0.08 X 0.010 | Dpmeas (dynes/cm$^2$) | 0.08 X 0.012 | Dpmeas (dynes/cm$^2$) |
|---|---|---|---|---|---|---|---|
| 41% HCT | Q=3.38 | 1.5 | 95.9 | 1.0 | 77.6 | 0.0 | 0.0 |
| 64% HCT | Q=3.38 | 4.0 | 255.8 | 3.0 | 232.9 | 2.0 | 182.1 |
| 41% HCT | Q=16.9 | 9.7 | 618.4 | 7.0 | 543.4 | 4.7 | 425.3 |
| 61% HCT | Q=16.9 | 20.7 | 1321.9 | 12.3 | 957.2 | 8.7 | 789.6 |

|  |  | 0.10 X 0.008 | Dpmeas (dynes/cm$^2$) | 0.10 X 0.010 | Dpmeas (dynes/cm$^2$) | 0.10 X 0.012 | Dpmeas (dynes/cm$^2$) |
|---|---|---|---|---|---|---|---|
| 41% HCT | Q=3.38 | 2.0 | 93.7 | 1.0 | 60.3 | 1.0 | 73.5 |
| 64% HCT | Q=3.38 | 4.5 | 210.8 | 3.0 | 180.9 | 2.0 | 146.9 |
| 41% HCT | Q=16.9 | 12.7 | 593.6 | 7.0 | 422.1 | 4.7 | 343.0 |
| 61% HCT | Q=16.9 | 23.3 | 1093.0 | 14.7 | 884.6 | 12.0 | 881.4 |

|  |  | 0.15 X 0.008 | Dpmeas (dynes/cm$^2$) | 0.15 X 0.010 | Dpmeas (dynes/cm$^2$) | 0.15 X 0.012 | Dpmeas (dynes/cm$^2$) |
|---|---|---|---|---|---|---|---|
| 41% HCT | Q=3.38 | 3.0 | 97.4 | 1.2 | 49.2 | 1.0 | 49.0 |
| 64% HCT | Q=3.38 | 6.5 | 211.0 | 3.5 | 143.5 | 2.0 | 97.9 |
| 41% HCT | Q=16.9 | 15.3 | 497.7 | 8.3 | 341.6 | 5.7 | 277.6 |
| 61% HCT | Q=16.9 | 35.7 | 1158.1 | 18.0 | 738.1 | 12.7 | 620.4 |

Signed and Sealed this

Thirty-first Day of December, 2002

JAMES E. ROGAN
*Director of the United States Patent and Trademark Office*